(12) United States Patent
Pang et al.

(10) Patent No.: US 11,169,128 B2
(45) Date of Patent: Nov. 9, 2021

(54) ELECTRONIC ID DATABASE AND DETECTION METHOD FOR PESTICIDE COMPOUND IN EDIBLE AGRO-PRODUCTS BASED ON LC-Q-ORBITRAP

(71) Applicants: CHINESE ACADEMY OF INSPECTION AND QUARANTINE, Beijing (CN); BEIJING UNI-STAR INSPECTION TECHNOLOGY CO., LTD., Beijing (CN)

(72) Inventors: Guofang Pang, Beijing (CN); Hui Chen, Beijing (CN); Qiaoying Chang, Beijing (CN); Kuiguo Han, Beijing (CN); Zijuan Zhang, Beijing (CN); Chunlin Fan, Beijing (CN); Xingqiang Wu, Beijing (CN); Ruobin Bai, Beijing (CN)

(73) Assignees: CHINESE ACADEMY OF INSPECTION AND QUARANTINE; BEIJING UNI-STAR INSPECTION TECHNOLOGY CO., LTD.

( * ) Notice: Subject to any disclaimer, the term of this patent is extended or adjusted under 35 U.S.C. 154(b) by 0 days.

(21) Appl. No.: 16/314,599

(22) PCT Filed: Dec. 14, 2018

(86) PCT No.: PCT/CN2018/121001
§ 371 (c)(1),
(2) Date: Dec. 31, 2018

(87) PCT Pub. No.: WO2019/200947
PCT Pub. Date: Oct. 24, 2019

(65) Prior Publication Data
US 2021/0223219 A1    Jul. 22, 2021

(30) Foreign Application Priority Data

Apr. 16, 2018   (CN) .......................... 201810337240.9
Nov. 19, 2018  (CN) .......................... 201811376380.3

(51) Int. Cl.
*G16C 20/90* (2019.01)
*G16C 20/40* (2019.01)
(Continued)

(52) U.S. Cl.
CPC .......... *G01N 30/8696* (2013.01); *G01N 30/06* (2013.01); *G01N 30/7233* (2013.01);
(Continued)

(58) Field of Classification Search
CPC .......... G01N 30/8696; G01N 30/7233; G01N 30/06; G01N 2030/027; G16C 20/90; G16C 20/40
See application file for complete search history.

(56) References Cited

U.S. PATENT DOCUMENTS 10,153,146 B2   12/2018   Kwiecien et al. .. H01J 49/0036

FOREIGN PATENT DOCUMENTS

| CN | 105651917 | 6/2016 | ............. G01N 30/06 |
| CN | 105823832 | 8/2016 | ............. G01N 30/02 |

(Continued)

OTHER PUBLICATIONS

International Search Report (w/ English translation) and Written Opinion issued in PCT/CN2018/121001, dated Mar. 14, 2019, 14 pages.

*Primary Examiner* — Jennifer Wecker
*Assistant Examiner* — Michael Paul Shimek
(74) *Attorney, Agent, or Firm* — Hayes Soloway P C.

(57) ABSTRACT

Disclosed is an electronic ID database and detection method for pesticide compound in edible agro-products based on
(Continued)

LC-Q-Orbitrap. The electronic ID database includes a collection of various pesticides compound electronic ID information, intelligent matching values and collision energies. It is ordered according to the retention time in the electronic ID. The electronic ID contains pesticide compounds information, retention time, adduct ions information, fragment ions information, collision energies, and the optimal full scan mass spectrum. The detection method includes sample pre-treatment, setting LC-Q-Orbitrap operating conditions and sample pesticide residue screening. Setting LC-Q-Orbitrap operating conditions contain setting suitable chromatography and mass spectrometry conditions. In pesticide residue screening procedures, firstly, the retention time is used to find pesticide compounds electronic ID database. If matching, the corresponding electronic ID information is extracted. Then the intelligent matching value is compared, if it is same, the result is recorded and displayed, and the screening is completed.

8 Claims, 3 Drawing Sheets

(51) Int. Cl.
*G01N 30/06* (2006.01)
*G01N 30/86* (2006.01)
*G01N 30/72* (2006.01)
*G01N 30/02* (2006.01)

(52) U.S. Cl.
CPC ............. *G16C 20/40* (2019.02); *G16C 20/90* (2019.02); *G01N 2030/027* (2013.01)

(56) References Cited

FOREIGN PATENT DOCUMENTS

| | | | |
|---|---|---|---|
| CN | 107077592 | 8/2017 | ............... G06K 9/00 |
| CN | 107085049 | 8/2017 | ............. G01N 30/02 |
| CN | 108760909 | * 11/2018 | ............. G01N 30/02 |
| EP | 2927691 | 10/2015 | ........... G01N 33/569 |

* cited by examiner

ELECTRONIC ID DATABASE AND DETECTION METHOD FOR PESTICIDE COMPOUND IN EDIBLE AGRO-PRODUCTS BASED ON LC-Q-ORBITRAP

TECHNICAL FIELD

The present invention relates to electronic ID database and detection method for pesticide compound in edible agro-products based on LC-Q-Orbitrap. It could achieve a non-targeted, multiple indexes and rapid screening for more than 500 pesticide residues in edible agro-products.

BACKGROUND ART

As early as 1976, the world health organization (WHO), Food and Agriculture Organization (FAO) and the United Nations Environment Programme (UNEP) established the Global Environment Monitoring System/Food (GEMS/Food) jointly to know Food contamination status of member nations, to understand the intake of food contaminants, to protect human health and to promote trade development. Nowadays, all countries in the world have raised the food safety issue to national security strategic position. Pesticide residue limit is one of food safety standards, and a threshold of international trade. Meanwhile, the requirements for pesticide residues show a growing trend of more and more varieties, and the limit is becoming more and more strict, that is, the threshold for pesticide residue set in international trade is getting higher and higher. For example, European Union (EU), Japan and USA have formulated 169,068 (481 pesticides), 44,340 (765 pesticides), and 13,055 (395 pesticides) pesticide residue limit standards, respectively. In 2016, China issued 4,140 MRLs related to 433 pesticides. At present, the uniform standard limit commonly used in the world is 10 μg/kg. Therefore, high-throughput rapid pesticide residue detection technique is needed for food safety and international trade, undoubtedly this also provide the opportunity and challenge to pesticide residue detection researchers. Among various pesticide residues analysis techniques, chromatographic-mass spectrometric technique is the most feasible method for high-throughput rapid multi-residue detection.

Presently, pesticide residue analysis techniques are mainly gas chromatography, liquid chromatography, gas chromatography-mass spectrometry and liquid chromatography-mass spectrometry etc. These techniques need pesticide reference materials as qualitative comparison. For example, 100 pesticide reference materials are needed as control if there are 100 pesticides to be detected, other pesticides might be missed. In the actual work of pesticide residue detection laboratories, most laboratories do not store hundreds of pesticide reference materials. The reason is that pesticide reference materials are not only expensive, but also valid for only 2 or 3 years, requiring repeated investment. There are only dozens of pesticide reference materials in the laboratory, and the number of pesticides that are routinely monitored is limited to these pesticides, resulting in food safety monitoring loopholes.

After in-depth research for many years, the inventors' team develops an accurate mass spectrum database including over 500 pesticides and pesticide residue screening method based on LC-Q-Orbitrap. This technique realizes rapid screening over 500 pesticide residues simultaneously in edible agro-products without pesticide reference materials as control and meets the current urgent requirement of high-throughput rapid detection of pesticide residue.

Contents of the Invention

The present invention develops an electronic ID database and detection method for pesticide compound in edible agro-products based on high-throughput high-resolution liquid new technique of chromatography-quadrupole-electrostatic field orbitrap mass spectrometry (LC-Q-Orbitrap), regarding present problems in pesticide residues screening technique which cannot achieve simultaneous multi-residue rapid screening. It can realize over 500 pesticide residue reference materials rapid screening without pesticide reference materials as control and meet the urgent need on high-throughput rapid detection method for pesticide residues in agro-products.

The invention adopts the following technical solutions:

an electronic ID database for pesticide compound based on LC-Q-Orbitrap includes various pesticide compounds electronic ID, which comprises pesticide compound information, retention time, adduct ion information, fragment ions information, collision energies and the optimal full scan mass spectrum;

the pesticide compound information includes the compound name and its molecular formula;

the retention time of the pesticide compound is detected under specific chromatography mass spectrometry condition by LC-Q-Orbitrap equipment under Full MS/dd-MS$^2$ mode, the pesticide compounds ion forms (+H, +NH$_4$, +Na) under ESI source and chemical formula are determined to get the accurate mass number of the pesticide compound adduct ion;

collecting full scan mass spectrum of fragment ions under multiple different collision energies; selecting the optimal full scan mass spectrum which contain plenty ions information, the optimal full scan mass spectrum refers that the abundance ratio of adduct ion is 10-20%, 3 to 5 fragment ions having the largest ion abundance ratio in the optimal full scan mass spectrum are selected, and the collision energy value is recorded;

the fragment ions information includes theoretical accurate mass number and ion abundance ratio in the optimal full scan mass spectrum;

the ion abundance ratio is the signal strength ratio between fragment ion and the signal strongest fragment ion;

the database is ordered according to the retention time in the electronic ID. Furthermore, the electronic ID database including intelligent matching model, the model in the electronic ID adds the intelligent matching value $P_m$, the calculation model is:

$$P_m = W_b M_b + W_q \cdot \sum_{i=1}^{n-1} (M_i \cdot W_i);$$

$$W_i = \frac{I_i - I_{i+1}}{I_1 - I_{n-1}};$$

$$W_b + W_q = 1;$$

wherein $M_b$ is the theoretical accurate mass number value of base peak ion, i.e. adduct ion, $M_i$ is the accurate mass number value of the i$^{th}$ confirmation ion, i.e. fragment ion, $W_i$ is the weight of the i$^{th}$ fragment ion, $I_i$ is the ion abundance ratio of $i^{th}$ fragment ion, the order of fragment ions is descending according to the abundance ratio, $W_b$ is the weight of the base peak ion, i.e. adduct ion, $W_q$ is the comprehensive weight of fragment ions, n is the number of fragment ions Furthermore, the values of $W_b$, $W_q$ could be adjusted according to intelligent matching model, generally $W_b=W_q=0.5$.

Furthermore, the detection method of theoretical accurate mass number of fragment ions is:

1) according to the compound molecular formula, the element composition of fragment ion is identified;
2) according to the mass number M of the fragment ion in the mass spectrum, the possible element composition list of the fragment ion could be obtained by calculation;

$$M = \sum_{i=1}^{n} X_i y_i$$

wherein, $X_i$ is the accurate mass number of the $i^{th}$ fragment ion, n is the element number of fragment ions, $y_i$ is the number of the corresponding element in the $i^{th}$ fragment ion 3) through the molecular structure cracking mechanism, selecting a reasonable fragment ion element composition from the list of fragment ion element composition, and the theoretical accurate mass number M' could be calculated.

$$M'=X_1 y'_1 + X_2 y'_2 + \ldots + X_n y'_n$$

wherein, $X_1, X_2 \ldots X_n$ are the accurate mass number of the fragment ion elements, $y'_1, y'_2 \ldots y'_n$ are the numbers of the corresponding elements of preferred fragment ion element composition.

Furthermore, the chromatography mass spectrometry conditions are:

Chromatography conditions: separation through liquid chromatography system, which is equipped with reversed phase column (Accucore aQ 150×2.1 mm, 2.6 μm); mobile phase solution A: 5 mM ammonium acetate-0.1% formic acid-water; mobile phase solution B: 0.1% formic acid-methanol; gradient elution program: 0 min: 1% B, 3 min: 30% B, 6 min: 40% B, 9 min: 40% B, 15 min: 60% B, 19 min: 90% B, 23 min: 90% B, 23.01 min: 1% B, post run for 4 min flow rate: 0.4 mL/min; column temperature: 40° C.; injection volume: 5 μL;

Mass spectrometry conditions: scan mode: Full MS/dd-MS$^2$; Full MS mass scan range: 70-1050 m/z; Resolution: 70,000, Full MS; 17,500, MS/MS; AGC: Full MS, 1e6; MS/MS, 1e5; Max IT: Full MS, 200 ms; MS/MS, 60 ms; Loop count: 1; MSX count: 1; Isolation width: 2.0 m/z; NCE(Stepped NCE): 40(50%); Under fill ratio: 1%; Apex trigger: 2-6 s; Dynamic Exclusion: 5 s; the mass spectrometry results is collected and processed by software TraceFinder.

A detection method for pesticide compound in edible agro-products based on LC-Q-Orbitrap includes:

1) the sample to be tested is homogenized by acidified acetonitrile, dehydrated, centrifuged, concentrated, and then purified by solid phase extraction column(SPE), and the residual pesticide is eluted by acetonitrile+toluene, and concentrated and filtered to prepare a sample solution to be tested.

2) the chromatogram of the sample solution are acquired under the specific chromatography and mass spectrometry condition by LC-Q-Orbitrap under Full MS/dd-MS$^2$ mode.

3) the chromatogram and mass spectrum of the sample solution are acquired under the specific chromatography and mass spectrometry conditions by LC-Q-Orbitrap under Full MS/ddMS$^2$ mode, and then to obtain the retention time, accurate mass number information of adduct ion, the fragment ions and mass spectrum under the corresponding optimal collision energy and record the electronic ID of unknown compounds corresponding to the retention time, 4) the electronic ID unknown compounds is sequentially compared with each electronic ID of pesticide compound in electronic ID database, if $\Delta T \leq 0.3$ and $\Delta P \leq 10\%$, the pesticide compound will be recorded, if $\Delta T \leq 0.3$ and $10\% < \Delta P \leq 30\%$, whether the pesticide compound is included or not is judged by the comparison of height and overlap ratio of the mass spectrum peak in the mass spectrum .otherwise it will be compared with the next electronic ID unknown compounds.

5) after detection is completed, the information of the pesticide contained in the test sample solution will be displayed.

wherein, $\Delta T$ is the absolute value of difference between the retention time of unknown compound and that of any pesticide compound in the database;

$$\Delta P = \frac{|P_c - P_i|}{\min(P_c, P_i)}$$

wherein, $P_c$ is the intelligent matching value of the unknown compound, $P_i$ is the intelligent matching value of the any pesticide compound in the database.

Furthermore, the sample also include the following pretreatment:

weigh 10.0 g (accurate to 0.01 g) of sample to 100 mL centrifuge tube, add 30-40 mL acidified acetonitrile, homogenize at 10,000-11,000 rpm for 1-2 min, add anhydrous magnesium sulfate and sodium chloride (mass ratio 4/1), the centrifuge tube was shaken for 8-10 min, and then centrifuged at 4200 rpm for 5-7 min, take 15-20 mL of supernatants into 150 mL heart-shaped bottle, and evaporate to 1-2 mL on a rotary evaporator at 40° C. water bath for clean-up.

CarbonNH$_2$ column was used, add 1-2 cm height anhydrous sodium sulfate into CarbonNH$_2$ column, SPE column was prewashed with 5-6 mL of acetonitrile/toluene solution, tap purification column gently to remove bubble, discard the effluent under the purification column. when the liquid level is slightly above the top of sodium sulfate, transfer the concentrate to the purification column with a 50 ml heart-shaped bottle under it, the heart-shaped bottle was rinsed with 2-3 mL of acetonitrile/toluene solution, and decant it to the purification column, repeat 2 to 3 times, the purification column was connected with a 25 mL reservoir there above and eluted with 25-30 mL of acetonitrile/toluene solution. The entire volume of effluent was collected and concentrated to 0.5 ml, and then evaporated it to dryness by nitrogen. Finally, after adding 1 mL of acetonitrile/water solution, it was sonicated and filtered through a 0.22 μm nylon membrane.

Beneficial Effects of the Present Invention:

1. Acquiring pesticide compounds electronic ID information by LC-Q-Orbitrap technique, and innovatively establishing electronic ID database of over 500 pesticides with 0.00001 m/z accurate mass by using electronic ID information to form a pesticide compound electronic ID database. Electronic reference materials replace the pesticide reference materials. It realizes the high-precision, high-efficiency and resource-saving non-targeted pesticide residue detection, the traditional identification method using pesticide reference materials as control was replaced with the electronic standard screening method using pesticide electronic ID and achieved a milestone in the development of non-targeted pesticide residue detection technology.

2 Taking compound mass spectrum information of high resolution accurate mass number and ion abundance ratio etc. as identification standards, innovatively establish the LC-Q-Orbitrap for screening and confirmation of over 500 pesticides based on pesticide electronic ID database. This technology has completely changed the original qualitative model with reference to compound reference materials. It is a new technology for rapid detection, high throughput, accurate and reliable pesticide residue detection without reference materials control. The reference materials as control was canceled, and the electronic standard identification was used to realize the replacement of the traditional method of the physical reference materials with electronic ID, and also realize the leap-forward development from targeted detection to non-targeted screening. It is resource-saving, pollution-reducing, analysis speed increasing, and achieves the requirement of green development, environment friendliness, clean and high efficacy.

3. The LC-Q-Qrbitrap pesticide residue screening method established in the present invention could retrieve and compare the corresponding information of the compound from the pesticide compound electronic ID database according to the information of the retention time, accurate mass number, ion abundance ratio, collision energy etc. of the target compound. Qualitative screening of pesticide is achieved based on the matching condition of target compound. The collision energy is added in the database innovatively, the acquisition and data extraction of the optimal full scan mass spectrum are realized by adjusting the collision energy to improve the accuracy of the data. When selecting the optimal collision energy, the mass spectrum with adduct ion abundance ratio of 10-20% was selected as the optimal mass spectrum, which can guarantee fragment ions formed from collision of adduct ion and the existence of adduct ion.

4. The LC-Q-Orbitrap pesticide residue screening method established by the present invention adopts Full MS/dd-MS$^2$ mode to analyze after injection of sample. Chromatogram and mass spectrum of over 500 pesticides can be acquired under the specific chromatography and mass spectrometry conditions for one sample injection. It shortens the analysis time and improves the sample detection efficiency.

5. Over 500 pesticides can be screening simultaneously by LC-Q-Orbitrap established in the present invention. The sensitivity of 80% of the pesticides is lower than the uniform standard 10 μg/kg, which meets the requirement of various countries' pesticide MRLs. The mass accuracy of this screening technique is lower than 5 ppm, it greatly decreases the false positive result and meets the requirement of multi-residue and high precision pesticide residue screening method.

6. This invention can rapidly calculate the intelligent matching value of each compound after quick auto-comparison. The intelligent matching value considers both the accurate mass number and ion abundance ratio information. It can stress the effect of the larger difference ion fragment according to the differentiated ion abundance ratio between the adduct ion and different fragment ions. The introduction of intelligent matching values changes the original deficiencies based on human judgment, enabling accurate automatic matching and realizing automatic detection.

EMBODIMENTS

This invention will be presented in detail with reference to drawings and embodiments.

Figure 1:
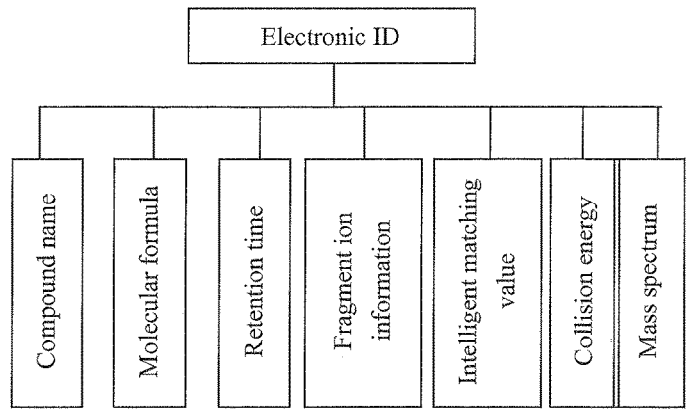
FIG. 1 LC-Q-Orbitrap pesticide compound electronic ID database model

Construction flow of LC-Q-Orbitrap pesticide contamination compound mass spectrum database is shown in FIG. 1, which is described in detail in Contents of the Invention. Next, the establishment procedure of pesticide compound electronic ID will be introduced in detail using Benalaxyl as an example.

Chromatography conditions: separation through liquid chromatography system, which is equipped with reversed phase column (Accucore aQ 150×2.1 mm, 2.6 μm); mobile phase solution A: 5 mM ammonium acetate-0.1% formic acid-water; mobile phase solution B: 0,1% formic acid-methanol; gradient elution program: 0 min. 1% B, 3 min: 30% B, 6 min: 40% B, 9 min: 40% B, 15 min: 60% B, 19 min: 90% B, 23 min: 90% B, 23.01 min: 1% B, post run for 4 min. flow rate: 0.4 mL/min; column temperature: 40° C.; injection volume: 5 μL.

Mass spectrometry conditions: scan mode: Full MS-ddMS$^2$; Full MS mass scan range:70-1050 m/z; Resolution: 70,000, Full MS; 17,500, MS/MS; AGC: Full MS, 1e6; MS/MS, 1e5; Max IT: Full MS, 200 ms; MS/MS, 60 ms; Loop count: 1; MSX count: 1; Isolation width: 2.0 m/z; NCE(Stepped NCE): 40(50%); Under fill ratio: 1%; Apex trigger: 2-6 s; Dynamic Exclusion: 5 s; the mass spectrometry results is collected and processed by software TraceFinder.

Figure 2:
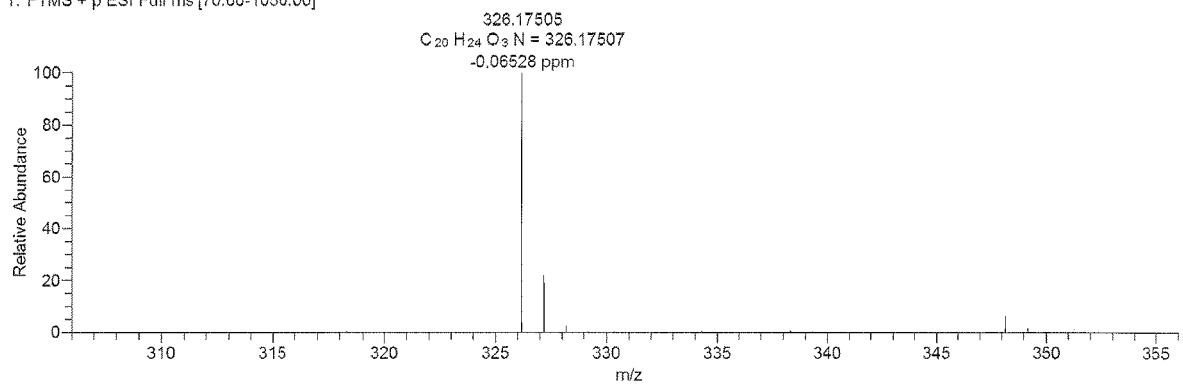
FIG. 2 The [M+H]$^+$ MS$^1$ spectrum of Benalaxyl
Figure 3:
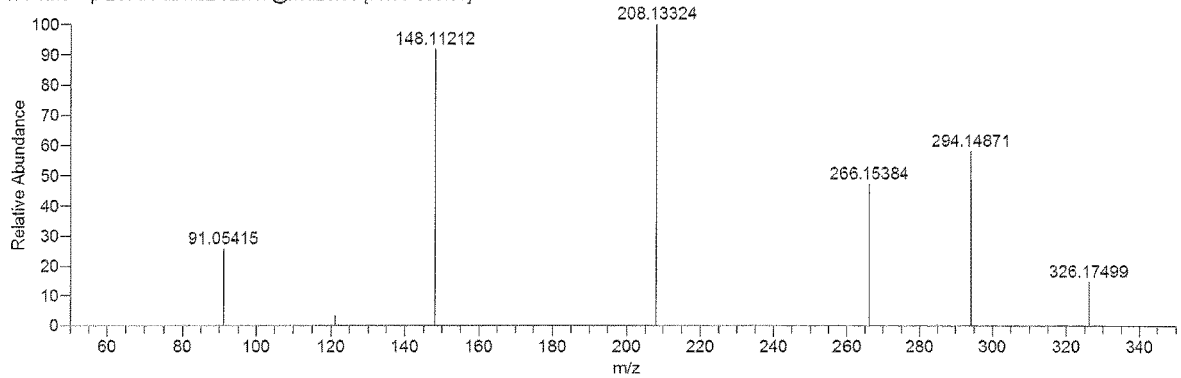
FIG. 3 The typical [M+H]$^+$ MS$^2$ spectrum of Benalaxyl when normalized collision energy (NCE) is 20.
Figure 4:
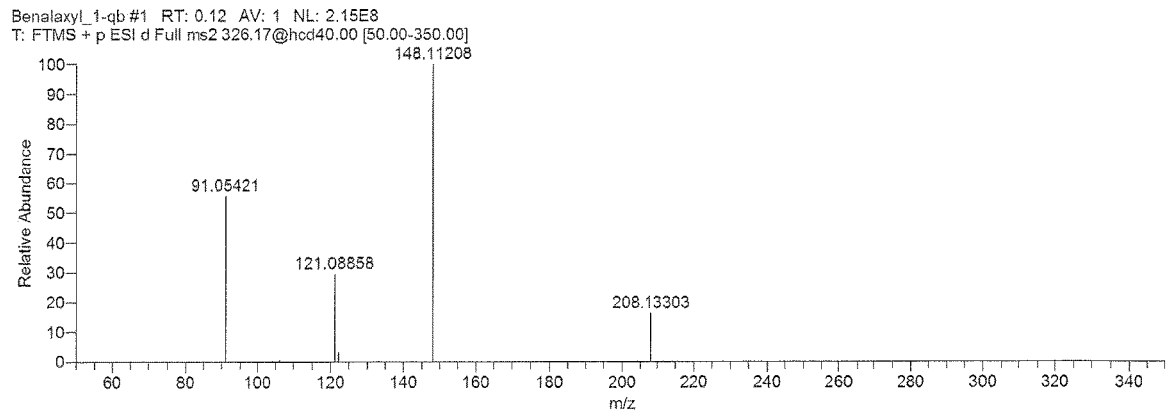
FIG. 4 The typical [M+H]$^+$ MS$^2$ spectrum of Benalaxyl when normalized collision energy (NCE) is 40.
Figure 5:
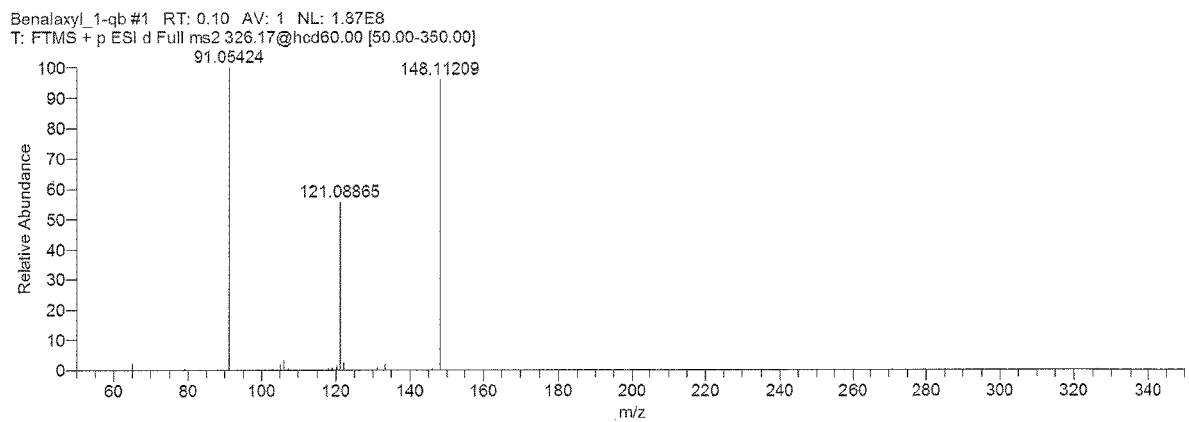
FIG. 5 The typical [M+H]$^+$ MS$^2$ spectrum of Benalaxyl when normalized collision energy (NCE) is 60
Figure 6:
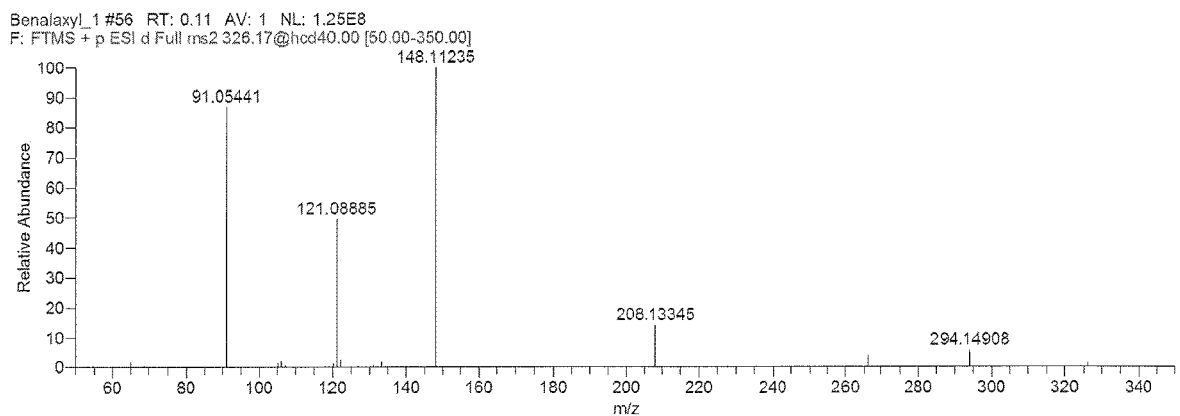
FIG. 6 The typical [M+H]$^+$ MS$^2$ spectrum of Benalaxyl when stepped normalized collision energies (NCE) are 20, 40 and 60.

The solvent standard is run under Full MS/dd-MS$^2$ mode, its molecular formula is $C_{20}H_{23}NO_3$, its MS$^1$ information is extracted and its [M+H]$^+$ adduct ion peak is found, it accurate mass number is 326.17507 (shown in FIG. 2). The acquisition methods are run when normalized collision energy (NCE) is 20 (FIG. 3), 40 (FIG. 4), 60 (FIG. 5), and stepped NCEs are 20, 40 and 60 (FIG. 6) respectively to collect Benalaxyl MS$^2$ fragment ions. According to chemical properties of Benalaxyl and combining with its MS$^2$ spectra under different NCEs, it is inferred that its 5 actual determined MS$^2$ fragment ions are 148.11212, 91.05415, 121.08865, 208.13303 and 294.14871. Combined with its chemical structure and formula information, the theoretical accurate values of 5 $MS^2$ fragments are determined, they are 148.11208 ($C_{10}H_{14}N$, abundance ratio 100.00%), 91.05423 ($C_7H_7$, abundance ratio 85.34%), 121.0886 ($C_8H_{11}N$, abundance ratio 47.17%), 208.13364 ($C_{12}H_{18}O_2N$, abundance ratio 13.40%) and 294.14886 ($C_{19}H_{20}O_2N$, abundance ratio 5.65%). The intelligent matching value $P_m$ of Benalaxyl is calculated as:

$$P_m = 0.5 \times 326.17507 +$$
$$0.5 \times \left( \frac{100 - 85.34}{100 - 5.65} \times 148.11208 + \frac{85.34 - 47.17}{100 - 5.65} \times 91.05423 + \right.$$
$$\frac{47.17 - 13.40}{100 - 5.65} \times 121.0886 +$$
$$\left. \frac{13.40 - 5.65}{100 - 5.65} \times 294.14886 = 219.30015 \right.$$

Benalaxyl electronic ID will be established and stored in electronic ID database, as shown in FIG. 1

Figure 7:
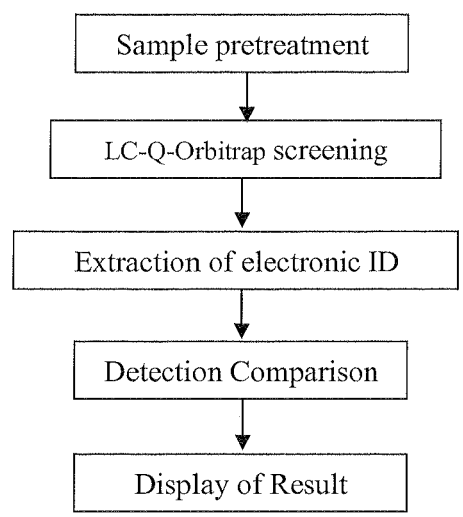
FIG. 7 Pesticide residue screening flow by LC-Q-Orbitrap.

As shown in FIG. 7, the method of electronic pesticide detection proposed in this invention can realize simultaneous determination of 500 pesticide residues by one-time sample preparation. The reference materials as control was canceled, and the electronic standard identification was used to realize the replacement of the traditional method of the physical reference materials with electronic ID, and also realize the leap-forward development from targeted detection to non-targeted screening. It is resource-saving, pollution-reducing, analysis speed increasing, and achieves the requirement of green development, environment friendliness, clean and high efficacy.

Table 1 shows the examples of 5 representative pesticide compound electronic ID in LC-Q-Orbitrap electronic ID database (excluding molecular formula). Table 2 shows over 500 pesticides list in LC-Q-Orbitrap electronic ID database.

TABLE 1

Example of 5 representative pesticides electronic ID in LC-Q-Orbitrap electronic ID database (excluding molecular formula)

| Compound Name | Type | MS Order | m/z | Relative ratio | NCE | $P_m$ | Adduct | Retention Time(min) |
|---|---|---|---|---|---|---|---|---|
| 1,3-Diphenyl urea | TargetPeak | ms1 | 213.102 | | 40 | 153.78782 | M + H | 10.33 |
| 1,3-Diphenyl urea | Fragment | ms2 | 94.0651 | 100% | | | M + H | 10.33 |
| 1,3-Diphenyl urea | Fragment | ms2 | 120.044 | 3.49% | | | M + H | 10.33 |
| 1,3-Diphenyl urea | Fragment | ms2 | 77.0386 | 1.24% | | | M + H | 10.33 |
| 1,3-Diphenyl urea | Fragment | ms2 | 67.0542 | 0.2% | | | M + H | 10.33 |
| 2.3.5-Trimethacarb | TargetPeak | ms1 | 194.118 | | 60 | 165.4111 | M + H | 12.653 |
| 2.3.5-Trimethacarb | Fragment | ms2 | 137.096 | 100% | | | M + H | 12.653 |
| 2.3.5-Trimethacarb | Fragment | ms2 | 119.086 | 3% | | | M + H | 12.653 |
| 2.3.5-Trimethacarb | Fragment | ms2 | 107.049 | 2.36% | | | M + H | 12.653 |
| 2.3.5-Trimethacarb | Fragment | ms2 | 121.065 | 1.75% | | | M + H | 12.653 |
| 2.3.5-Trimethacarb | Fragment | ms2 | 91.0542 | 1.2% | | | M + H | 12.653 |
| 3-indolyl | TargetPeak | ms1 | 176.071 | | 40 | 149.61321 | M + H | 5.78 |
| 3-indolyl | Fragment | ms2 | 120.081 | 100% | | | M + H | 5.78 |
| 3-indolyl | Fragment | ms2 | 130.066 | 55.19% | | | M + H | 5.78 |
| 3-indolyl | Fragment | ms2 | 84.9598 | 35.25% | | | M + H | 5.78 |
| 3,4,5-Trimethacarb | TargetPeak | ms1 | 194.118 | | 60 | 163.60052 | M + H | 12.96 |
| 3,4,5-Trimethacarb | Fragment | ms2 | 137.096 | 100% | | | M + H | 12.96 |
| 3,4,5-Trimethacarb | Fragment | ms2 | 122.073 | 21.03% | | | M + H | 12.96 |
| 3,4,5-Trimethacarb | Fragment | ms2 | 109.101 | 11.02% | | | M + H | 12.96 |
| 3,4,5-Trimethacarb | Fragment | ms2 | 119.086 | 3.08% | | | M + H | 12.96 |
| 3,4,5-Trimethacarb | Fragment | ms2 | 95.0491 | 1.92% | | | M + H | 12.96 |
| 4-(3-indolyl)-butyric acid | TargetPeak | ms1 | 204.102 | | 40 | 191.71951 | M + H | 9.31 |
| 4-(3-indolyl)-butyric acid | Fragment | ms2 | 186.091 | 35.39% | | | M + H | 9.31 |
| 4-(3-indolyl)-butyric acid | Fragment | ms2 | 144.081 | 10.25% | | | M + H | 9.31 |
| 4-(3-indolyl)-butyric acid | Fragment | ms2 | 168.081 | 6.05% | | | M + H | 9.31 |
| 4-(3-indolyl)-butyric acid | Fragment | ms2 | 130.065 | 4.12% | | | M + H | 9.31 |

TABLE 2

Over 500 pesticides list

| No. | Compound Name | CAS No. | ChemicalFormula | $t_R$ (min) | Adduct | Precursor |
|---|---|---|---|---|---|---|
| 1 | 1,3-Diphenyl urea | 102-07-8 | C13H12N2O | 10.33 | M + H | 213.10224 |
| 2 | 1-naphthyl acetamide | 86-86-2 | C12H11NO | 7.05 | M + H | 186.09134 |
| 3 | 2,6-Dichlorobenzamide | 2008-58-4 | C7H5Cl2NO | 3.76 | M + H | 189.9821 |
| 4 | 3.4.5-Trimethacarb | 2686-99-9 | C11H15NO2 | 12.39 | M + H | 194.11756 |
| 5 | 6-benzylaminopurine | 1214-39-7 | C12H11N5 | 6.03 | M + H | 226.10872 |
| 6 | 6-chloro-4-hydroxy-3-phenyl-pyridazin | 40020-01-7 | C10H7ClN2O | 6.16 | M + H | 207.03197 |
| 7 | Abamectin | 71751-41-2 | C48H72O14 | 20.06 | M + NH4 | 890.52603 |
| 8 | Acephate | 30560-19-1 | C4H10NO3PS | 2.44 | M + H | 184.01918 |
| 9 | Acetamiprid | 135410-20-7 | C10H11ClN4 | 5.1 | M + H | 223.0745 |
| 10 | Acetamiprid-N-desmethyl | 190604-92-3 | C9H9ClN4 | 4.88 | M + H | 209.05885 |
| 11 | Acetochlor | 34256-82-1 | C14H20ClNO2 | 16.72 | M + H | 270.12553 |
| 12 | Aclonifen | 74070-46-5 | C12H9ClN2O3 | 17.62 | M + H | 265.03745 |
| 13 | Albendazole | 54965-21-8 | C12H15N3O2S | 12.33 | M + H | 266.09577 |
| 14 | Aldicarb | 116-06-3 | C7H14N2O2S | 6.21 | M + NH4 | 208.11142 |

TABLE 2-continued

Over 500 pesticides list

| No. | Compound Name | CAS No. | ChemicalFormula | $t_R$ (min) | Adduct | Precursor |
|---|---|---|---|---|---|---|
| 15 | Aldicarb sulfone | 1646-88-4 | C7H14N2O4S | 3.21 | M + NH4 | 240.10125 |
| 16 | Aldicarb-sulfoxide | 1646-87-3 | C7H14N2O3S | 3.05 | M + H | 207.07979 |
| 17 | Aldimorph | 91315-15-0 | C18H37NO | 21.73 | M + H | 284.29479 |
| 18 | Allidochlor | 93-71-0 | C8H12ClNO | 6.59 | M + H | 174.06802 |
| 19 | Ametoctradin | 865318-97-4 | C15H25N5 | 18.31 | M + H | 276.21827 |
| 20 | Ametryn | 834-12-8 | C9H17N5S | 11.44 | M + H | 228.12774 |
| 21 | Amicarbazone | 129909-90-6 | C10H19N5O2 | 7.5 | M+ | 143.09274 |
| 22 | Amidithion | 919-76-6 | C7H16NO4PS2 | 5.88 | M + H | 274.03311 |
| 23 | Amidosulfuron | 120923-37-7 | C9H15N5O7S2 | 9.27 | M + H | 370.04857 |
| 24 | Aminocarb | 2032-59-9 | C11H16N2O2 | 2.9 | M + H | 209.12845 |
| 25 | Aminopyralid | 150114-71-9 | C6H4Cl2N2O2 | 1.77 | M + H | 206.97226 |
| 26 | Amitraz | 33089-61-1 | C19H23N3 | 19.71 | M + H | 294.19647 |
| 27 | Amitrole | 61-82-5 | C2H4N4 | 0.77 | M + H | 85.05087 |
| 28 | Ancymidol | 12771-68-5 | C15H16N2O2 | 8.46 | M + H | 257.12845 |
| 29 | Anilofos | 64249-01-0 | C13H19ClNO3PS2 | 17.83 | M + H | 368.03053 |
| 30 | Aspon | 3244-90-4 | C12H28O5P2S2 | 19.73 | M + H | 379.09261 |
| 31 | Asulam | 3337-71-1 | C8H10N2O4S | 2.82 | M + H | 231.0434 |
| 32 | Athidathion | 19691-80-6 | C8H15N2O4PS3 | 16.42 | M + H | 331.00043 |
| 33 | Atratone | 1610-17-9 | C9H17N5O | 6.91 | M + H | 212.15059 |
| 34 | Atrazine | 1912-24-9 | C8H14ClN5 | 11.14 | M + H | 216.10105 |
| 35 | Atrazine-Desethyl | 6190-65-4 | C6H10ClN5 | 5.47 | M + H | 188.06975 |
| 36 | Atrazine-desisopropyl | 1007-28-9 | C5H8ClN5 | 4.17 | M + H | 174.0541 |
| 37 | Azaconazole | 60207-31-0 | C12H11Cl2N3O2 | 12.91 | M + H | 300.03011 |
| 38 | Azametbiphos | 35575-96-3 | C9H10ClN2O5PS | 7.5 | M + H | 324.98093 |
| 39 | Azinphos-ethyl | 2642-71-9 | C12H16N3O3PS2 | 16.65 | M + H | 346.04435 |
| 40 | Azinphos-methyl | 86-50-0 | C10H12N3O3PS2 | 13.63 | M + H | 318.01305 |
| 41 | Aziprotryne | 4658-28-0 | C7H11N7S | 14.84 | M + H | 226.08694 |
| 42 | Azoxystrobin | 131860-33-8 | C22H17N3O5 | 15.04 | M + H | 404.1241 |
| 43 | Beflubutamid | 113614-08-7 | C18H17F4NO2 | 17.83 | M + H | 356.12682 |
| 44 | Benalaxyl | 71626-11-4 | C20H23NO3 | 17.86 | M + H | 326.17507 |
| 45 | Bendiocarb | 22781-23-3 | C11H13NO4 | 8.01 | M + H | 224.09173 |
| 46 | Benfuracarb | 82560-54-1 | C20H30N2O5S | 18.86 | M + H | 411.19482 |
| 47 | Benodanil | 15310-01-7 | C13H10INO | 11.13 | M + H | 323.98798 |
| 48 | Benomyl | 17804-35-2 | C14H18N4O3 | 0 | M + H | 291.14517 |
| 49 | Benoxacor | 98730-04-2 | C11H11Cl2NO2 | 13.34 | M + H | 260.02396 |
| 50 | Bensulfuron-methyl | 83055-99-6 | C16H18N4O7S | 14.08 | M + H | 411.0969 |
| 51 | Bensulide | 741-58-2 | C14H24NO4PS3 | 17.55 | M + H | 398.06778 |
| 52 | Bensultap | 17606-31-4 | C17H21NO4S4 | 12.96 | M + H | 432.04262 |
| 53 | Benthiavalicarb-isopropyl | 177406-68-7 | C18H24FN3O3S | 16.14 | M + H | 382.15952 |
| 54 | Benzofenap | 82692-44-2 | C22H20Cl2N2O3 | 18.77 | M + H | 431.09237 |
| 55 | Benzoximate | 29104-30-1 | C18H18ClNO5 | 18.23 | M + H | 364.09463 |
| 56 | Benzoylprop | 22212-56-2 | C16H13Cl2NO3 | 16.39 | M + H | 338.03453 |
| 57 | Benzoylprop-ethyl | 22212-55-1 | C18H17Cl2NO3 | 18.07 | M + H | 366.06583 |
| 58 | Bifenazate | 149877-41-8 | C17H20N2O3 | 16.6 | M + H | 301.15467 |
| 59 | Bioallethrin | 584-79-2 | C19H26O3 | 19.18 | M + H | 303.19547 |
| 60 | Bioresmethrin | 28434-01-7 | C22H26O3 | 20.21 | M + H | 339.19547 |
| 61 | Bitertanol | 55179-31-2 | C20H23N3O2 | 18.17 | M + H | 338.1863 |
| 62 | Boscalid | 188425-85-6 | C18H12Cl2N2O | 15.39 | M + H | 343.03994 |
| 63 | Bromacil | 314-40-9 | C9H13BrN2O2 | 7.62 | M + H | 261.02332 |
| 64 | Bromfenvinfos | 33399-00-7 | C12H14BrCl2O4P | 18.11 | M + H | 402.92629 |
| 65 | Bromobutide | 74712-19-9 | C15H22BrNO | 16.84 | M + H | 312.09575 |
| 66 | Brompyrazon | 3042-84-0 | C10H8BrN3O | 5.13 | M + H | 265.99235 |
| 67 | Bromuconazole | 116255-48-2 | C13H12BrCl2N3O | 17.43 | M + H | 375.96136 |
| 68 | Bupirimate | 41483-43-6 | C13H24N4O3S | 16.06 | M + H | 317.16419 |
| 69 | Buprofezin | 69327-76-0 | C16H23N3OS | 18.75 | M + H | 306.16346 |
| 70 | Butachlor | 23184-66-9 | C17H26ClNO2 | 19.18 | M + H | 312.17248 |
| 71 | Butafenacil | 134605-64-4 | C20H18ClF3N2O6 | 16.86 | M + NH4 | 492.11437 |
| 72 | Butamifos | 36335-67-8 | C13H21N2O4PS | 18.21 | M + H | 333.10324 |
| 73 | Butocarboxim | 34681-10-2 | C7H14N2O2S | 6.09 | M + Na | 213.06682 |
| 74 | Butocarboxim sulfoxide | 34681-24-8 | C7H14N2O3S | 2.89 | M + H | 207.07979 |
| 75 | Butoxycarboxim | 34681-23-7 | C7H14N2O4S | 3.13 | M + H | 223.0747 |
| 76 | Butralin | 33629-47-9 | C14H21N3O4 | 19.68 | M + H | 296.16048 |
| 77 | Butylate | 2008-41-5 | C11H23NOS | 18.82 | M + H | 218.15731 |
| 78 | Cadusafos | 95465-99-9 | C10H23O2PS2 | 18.44 | M + H | 271.09498 |
| 79 | Cafenstrole | 125306-83-4 | C16H22N4O3S | 16.28 | M + H | 351.14854 |
| 80 | Carbaryl | 63-25-2 | C12H11NO2 | 9.22 | M + H | 202.08626 |
| 81 | Carbendazim | 10605-21-7 | C9H9N3O2 | 3.79 | M + H | 192.07675 |
| 82 | Carbetamide | 16118-49-3 | C12H16N2O3 | 6.96 | M + H | 237.12337 |
| 83 | Carbofuran | 1563-66-2 | C12H15NO3 | 8.08 | M + H | 222.11247 |
| 84 | Carbofuran-3-hydroxy | 16655-82-6 | C12H15NO4 | 4.91 | M + H | 238.10738 |
| 85 | Carbophenothion | 786-19-6 | C11H6ClO2PS3 | 19.59 | M + H | 342.98113 |
| 86 | Carbosulfan | 55285-14-8 | C20H32N2O3S | 20.41 | M + H | 381.22064 |
| 87 | Carboxin | 5234-68-4 | C12H13NO2S | 8.78 | M + H | 236.07398 |
| 88 | Carfentrazone-ethyl | 128639-02-1 | C15H14Cl2F3N3O3 | 17.53 | M + NH4 | 429.07026 |
| 89 | Carpropamid | 104030-54-8 | C15H18Cl3NO | 17.87 | M + H | 334.05267 |
| 90 | Cartap | 15263-53-3 | C7H15N3O2S2 | 0.8 | M + H | 238.06784 |

TABLE 2-continued

Over 500 pesticides list

| No. | Compound Name | CAS No. | ChemicalFormula | $t_R$ (min) | Adduct | Precursor |
|---|---|---|---|---|---|---|
| 91 | Chlorantraniliprole | 500008-45-7 | C18H14BrCl2N5O2 | 13.84 | M + H | 481.97807 |
| 92 | Chlordimeform | 6164-98-3 | C10H13ClN2 | 4.08 | M + H | 197.084 |
| 93 | Chlorfenvinphos | 470-90-6 | C12H14Cl3O4P | 17.98 | M + H | 358.97681 |
| 94 | Chlorfluazuron | 71422-67-8 | C20H9Cl3F5N3O3 | 19.82 | M + H | 539.97024 |
| 95 | Chloridazon | 1698-60-8 | C10H8ClN3O | 4.91 | M + H | 222.04287 |
| 96 | Chlorimuron-ethyl | 90982-32-4 | C15H15ClN4O6S | 15.63 | M + H | 415.04736 |
| 97 | Chlormequat | 7003-89-6 | C5H13ClN | 0.79 | M+ | 122.0731 |
| 98 | Chlorotoluron | 15545-48-9 | C10H13ClN2O | 10.61 | M + H | 213.07892 |
| 99 | Chloroxuron | 1982-47-4 | C15H15ClN2O2 | 16.4 | M + H | 291.08948 |
| 100 | Chlorphonium | 115-78-6 | C19H32Cl3P | 15.89 | M+ | 361.16132 |
| 101 | Chlorphoxim | 14816-20-7 | C12H14ClN2O3PS | 18.2 | M + H | 333.0224 |
| 102 | Chlorpyrifos | 2921-88-2 | C9H11Cl3NO3PS | 19.36 | M + H | 349.93356 |
| 103 | Chlorpyrifos-methyl | 5598-13-0 | C7H7Cl3NO3PS | 18.43 | M + H | 321.90226 |
| 104 | Chlorsulfuron | 64902-72-3 | C12H12ClN5O4S | 9.66 | M + H | 358.03713 |
| 105 | Chlorthiophos | 60238-56-4 | C11H15Cl2O3PS2 | 19.64 | M + H | 360.965 |
| 106 | Chromafenozide | 143807-66-3 | C24H30N2O3 | 16.83 | M + H | 395.23292 |
| 107 | Cinmethylin | 87818-31-3 | C18H26O2 | 19.06 | M + H | 275.20056 |
| 108 | Cinosulfuron | 94593-91-6 | C15H19N5O7S | 7.56 | M + H | 414.1078 |
| 109 | Clethodim | 99129-21-2 | C17H26ClNO3S | 18.7 | M + H | 360.13947 |
| 110 | Clodinafop free acid | 114420-56-3 | C14H11ClFNO4 | 15.13 | M + H | 312.04334 |
| 111 | Clodinafop-propargyl | 105512-06-9 | C17H13ClFNO4 | 17.57 | M + H | 350.05899 |
| 112 | Clofentezine | 74115-24-5 | C14H8Cl2N4 | 18.41 | M + H | 303.01988 |
| 113 | Clomazone | 81777-89-1 | C12H14ClNO2 | 13.67 | M + H | 240.07858 |
| 114 | Clomeprop | 84496-56-0 | C16H15Cl2NO2 | 19.04 | M + H | 324.05526 |
| 115 | Cloquintocet-mexyl | 99607-70-2 | C18H22ClNO3 | 19.19 | M + H | 336.1361 |
| 116 | Cloransulam-methyl | 147150-35-4 | C15H13ClFN5O5S | 9.85 | M + H | 430.03827 |
| 117 | Clothianidin | 210880-92-5 | C6H8ClN5O2S | 4.42 | M + Fl | 250.016 |
| 118 | Coumaphos | 56-72-4 | C14H16ClO5PS | 17.92 | M + H | 363.02174 |
| 119 | Crotoxyphos | 7700-17-6 | C14H19O6P | 15.49 | M + NH4 | 332.12575 |
| 120 | Crufomate | 299-86-5 | C12H19ClNO3P | 17.35 | M + H | 292.08638 |
| 121 | Cumyluron | 99485-76-4 | C17H19ClN2O | 16.39 | M + H | 303.12587 |
| 122 | Cyanazine | 21725-46-2 | C9H13ClN6 | 7.27 | M + H | 241.0963 |
| 123 | Cyazofamid | 120116-88-3 | C13H13ClN4O2S | 16.99 | M + H | 325.05205 |
| 124 | Cycloate | 1134-23-2 | C11H21NOS | 18.4 | M + H | 216.14166 |
| 125 | Cyclosulfamuron | 136849-15-5 | C17H19N5O6S | 16.59 | M + H | 422.11288 |
| 126 | Cycluron | 2163-69-1 | C11H22N2O | 12.54 | M + H | 199.18049 |
| 127 | Cyflufenamid | 180409-60-3 | C20H17F5N2O2 | 18.32 | M + H | 413.1283 |
| 128 | Cymoxanil | 57966-95-7 | C7H10N4O3 | 5.28 | M + H | 199.08257 |
| 129 | Cyprazine | 22936-86-3 | C9H14ClN5 | 11.25 | M + H | 228.10105 |
| 130 | Cyproconazole | 94361-06-5 | C15H18ClN3O | 16.26 | M + H | 292.12112 |
| 131 | Cyprodinil | 121552-61-2 | C14H15N3 | 16.99 | M + H | 226.13387 |
| 132 | Cyprofuram | 69581-33-5 | C14H14ClNO3 | 9.99 | M + H | 280.0735 |
| 133 | Cyromazine | 66215-27-8 | C6H10N6 | 2.01 | M + H | 167.10397 |
| 134 | Daminozide | 1596-84-5 | C6H12N2O3 | 0.81 | M + H | 161.09207 |
| 135 | Dazomet | 533-74-4 | C5H10N2S2 | 3.31 | M + H | 163.03582 |
| 136 | Demeton-S | 126-75-0 | C8H19O3PS2 | 0 | M + H | 259.0586 |
| 137 | Demeton-S sulfoxide | 2496-92-6 | C8H19O4PS2 | 5.44 | M + H | 275.05351 |
| 138 | Demeton-S-methyl | 919-86-8 | C6H15O3PS2 | 8.24 | M + H | 231.0273 |
| 139 | Demeton-S-methyl sulfone | 17040-19-6 | C6H15O5PS2 | 3.78 | M + H | 263.01713 |
| 140 | Demeton-S-methyl sulfoxide | 301-12-2 | C6H15O4PS2 | 3.69 | M + H | 247.02221 |
| 141 | Desethyl-sebuthylazine | 37019-18-4 | C7H12ClN5 | 7.21 | M + H | 202.0854 |
| 142 | Desmedipham | 13684-56-5 | C16H16N2O4 | 13.49 | M + NH4 | 318.14483 |
| 143 | Desmethyl-pirimicarb | 30614-22-3 | C10H16N4O2 | 4.48 | M + H | 225.1346 |
| 144 | Desmetryn | 1014-69-3 | C8H15N5S | 8.13 | M + H | 214.11209 |
| 145 | Diafenthiuron | 80060-09-9 | C23H32N2OS | 19.78 | M + H | 385.23081 |
| 146 | Dialifos | 10311-84-9 | C14H17ClNO4PS2 | 18.36 | M + H | 394.00979 |
| 147 | Diallate | 2303-16-4 | C10H17Cl2NOS | 18.64 | M + H | 270.04807 |
| 148 | Diazinon | 333-41-5 | C12H21N2O3PS | 17.9 | M + H | 305.10833 |
| 149 | Dibutyl succinate | 141-03-7 | C12H22O4 | 17.59 | M + H | 231.15909 |
| 150 | Dichlofenthion | 97-17-6 | C10H13Cl2O3PS | 18.82 | M + H | 314.97728 |
| 151 | Diclobutrazole | 75736-33-3 | C15H19Cl2N3O | 17.56 | M + H | 328.09779 |
| 152 | Diclosulam | 145701-21-9 | C13H10Cl2FN5O3S | 10.81 | M + H | 405.99382 |
| 153 | Dicrotophos | 141-66-2 | C8H16NO5P | 4.35 | M + H | 238.08389 |
| 154 | Diethatyl-ethyl | 38727-55-8 | C16H22ClNO3 | 17.41 | M + H | 312.1361 |
| 155 | Diethofencarb | 87130-20-9 | C14H21NO4 | 14.36 | M + H | 268.15433 |
| 156 | Diethyltoluamide | 134-62-3 | C12H17NO | 12.19 | M + H | 192.13829 |
| 157 | Difenoconazole | 119446-68-3 | C19H17Cl2N3O3 | 18.49 | M + H | 406.07197 |
| 158 | Difenoxuron | 14214-32-5 | C16H18N2O3 | 12.91 | M + H | 287.13902 |
| 159 | Diflubenzuron | 35367-38-5 | C14H9ClF2N2O2 | 17.28 | M + H | 311.03934 |
| 160 | Dimefox | 115-26-4 | C4H12FN2OP | 4.38 | M + H | 155.0744 |
| 161 | Dimefuron | 34205-21-5 | C15H19ClN4O3 | 13.94 | M + H | 339.12184 |
| 162 | Dimepiperate | 61432-55-1 | C15H21NOS | 18.53 | M + H | 264.14166 |
| 163 | Dimethachlor | 50563-36-5 | C13H18ClNO2 | 12.96 | M + H | 256.10988 |
| 164 | Dimethametryn | 22936-75-0 | C11H21N5S | 16.56 | M + H | 256.15904 |
| 165 | Dimethenamid | 87674-68-8 | C12H18ClNO2S | 14.71 | M + H | 276.08195 |
| 166 | Dimethenamid-P | 163515-14-8 | C12H18ClNO2S | 14.62 | M + H | 276.08195 |

TABLE 2-continued

Over 500 pesticides list

| No. | Compound Name | CAS No. | ChemicalFormula | $t_R$ (min) | Adduct | Precursor |
|---|---|---|---|---|---|---|
| 167 | Dimethirimol | 5221-53-4 | C11H19N3O | 5.93 | M + H | 210.16009 |
| 168 | Dimethoate | 60-51-5 | C5H12NO3PS2 | 4.82 | M + H | 230.0069 |
| 169 | Dimethomorph | 110488-70-5 | C21H22ClNO4 | 15.39 | M + H | 388.13101 |
| 170 | Dimethylvinphos (Z) | 67628-93-7 | C10H10Cl3O4P | 16.33 | M + H | 330.9455 |
| 171 | Dimetilan | 644-64-4 | C10H16N4O3 | 5.4 | M + H | 241.12952 |
| 172 | Dimoxystrobin | 149961-52-4 | C19H22N2O3 | 17.42 | M + H | 327.17032 |
| 173 | Diniconazole | 83657-24-3 | C15H17Cl2N3O | 18.32 | M + H | 326.08214 |
| 174 | Dinitramine | 29091-05-2 | C11H13F3N4O4 | 18.1 | M + H | 323.09617 |
| 175 | Dinotefuran | 165252-70-0 | C7H14N4O3 | 2.97 | M + H | 203.11387 |
| 176 | Diphenamid | 957-51-7 | C16H17NO | 13.27 | M + H | 240.13829 |
| 177 | Dipropetryn | 4147-51-7 | C11H21N5S | 16.36 | M + H | 256.15904 |
| 178 | Disulfoton sulfone | 2497-06-5 | C8H19O4PS3 | 11.55 | M + H | 307.02558 |
| 179 | Disulfoton sulfoxide | 2497-06-7 | C8H19O3PS3 | 11.1 | M + H | 291.03067 |
| 180 | Ditalimfos | 5131-24-8 | C12H14NO4PS | 9.67 | M + H | 300.04539 |
| 181 | Dithiopyr | 97886-45-8 | C15H16F5NO2S2 | 18.8 | M + H | 402.06154 |
| 182 | Diuron | 330-54-1 | C9H10Cl2N2O | 12.28 | M + H | 233.02429 |
| 183 | Dodemorph | 1593-77-7 | C18H35NO | 20.75 | M + H | 282.27914 |
| 184 | Drazoxolon | 5707-69-7 | C10H8ClN3O2 | 16.58 | M + H | 238.03778 |
| 185 | Edifenphos | 17109-49-8 | C14H15O2PS2 | 17.76 | M + H | 311.03238 |
| 186 | Emamectin-benzoate | 119791-41-2 | C49H75NO13 | 19.3 | M + H | 886.53112 |
| 187 | Epoxiconazole | 106325-08-0 | C17H13ClFN3O | 16.95 | M + H | 330.08039 |
| 188 | Esprocarb | 85785-20-2 | C15H23NOS | 19.04 | M + H | 266.15731 |
| 189 | Elaconazole | 60207-93-4 | C14H15Cl2N3O2 | 16.89 | M + H | 328.06141 |
| 190 | Ethametsulfuron-methyl | 97780-06-8 | C15H18N6O6S | 10.98 | M + H | 411.10813 |
| 191 | Ethidimuron | 30043-49-3 | C7H12N4O3S2 | 4.47 | M + H | 265.04236 |
| 192 | Ethiofencarb | 29973-13-5 | C11H15NO2S | 9.6 | M + H | 226.08963 |
| 193 | Ethiofencarb sulfone | 53380-23-7 | C11H15NO4S | 4.28 | M + NH4 | 275.106 |
| 194 | Ethiofencarb sulfoxide | 53380-22-6 | C11H15NO3S | 4.47 | M + H | 242.08454 |
| 195 | Ethion | 563-12-2 | C9H22O4P2S4 | 19.22 | M + H | 384.99489 |
| 196 | Ethiprole | 181587-01-9 | C13H9Cl2F3N4OS | 15.18 | M + H | 396.9899 |
| 197 | Ethirimol | 23947-60-6 | C11H19N3O | 6.12 | M + H | 210.16009 |
| 198 | Ethoprophos | 13194-48-4 | C8H19O2PS2 | 16.79 | M + H | 243.06368 |
| 199 | Ethoxyquin | 91-53-2 | C14H19NO | 11.56 | M + H | 218.15394 |
| 200 | Ethoxysulfuron | 126801-58-9 | C15H18N4O7S | 15.97 | M + H | 399.0969 |
| 201 | Etobenzanid | 79540-50-4 | C16H15Cl2NO3 | 17.97 | M + H | 340.05018 |
| 202 | Etoxazole | 153233-91-1 | C21H23F2NO2 | 19.58 | M + H | 360.17696 |
| 203 | Etrimfos | 38260-54-7 | C10H17N2O4PS | 17.6 | M + H | 293.07194 |
| 204 | Famphur | 52-85-7 | C10H16NO5PS2 | 12.11 | M + H | 326.02803 |
| 205 | Fenamidone | 161326-34-7 | C17H17N3OS | 15.19 | M + H | 312.11651 |
| 206 | Fenamiphos | 22224-92-6 | C13H22NO3PS | 17.32 | M + H | 304.11308 |
| 207 | Fenamiphos sulfoxide | 31972-43-7 | C13H22NO4PS | 9.14 | M + H | 320.10799 |
| 208 | Fenamiphos-sulfone | 31972-44-8 | C13H22NO5PS | 9.75 | M + H | 336.10291 |
| 209 | Fenarimol | 60168-88-9 | C17H12Cl2N2O | 16.67 | M + H | 331.03994 |
| 210 | Fenazaquin | 120928-09-8 | C20H22N2O | 20.27 | M + H | 307.18049 |
| 211 | Fenbuconazole | 114369-43-6 | C19H17ClN4 | 17.23 | M + H | 337.12145 |
| 212 | Fenfuram | 24691-80-3 | C12H11NO2 | 8.41 | M + H | 202.08626 |
| 213 | Fenhexamid | 126833-17-8 | C14H17Cl2NO2 | 16.43 | M + H | 302.07091 |
| 214 | Fenobucarb | 3766-81-2 | C12H17NO2 | 14.17 | M + H | 208.13321 |
| 215 | Fenothiocarb | 62850-32-2 | C13H19NO2S | 17.35 | M + H | 254.12093 |
| 216 | Fenoxanil | 115852-48-7 | C15H18Cl2N2O2 | 17.45 | M + H | 329.08181 |
| 217 | Fenoxaprop-ethyl | 66441-23-4 | C18H16ClNO5 | 18.89 | M + H | 362.07898 |
| 218 | Fenoxaprop-P-Ethyl | 71238-80-2 | C18H16ClNO5 | 18.89 | M + H | 362.07898 |
| 219 | Fenoxycarb | 72490-01-8 | C17H19NO4 | 17.45 | M + H | 302.13868 |
| 220 | Fenpropidin | 67306-00-7 | C19H31N | 13.97 | M + H | 274.25293 |
| 221 | Fenpropimorph | 67564-91-4 | C20H33NO | 14.49 | M + H | 304.26349 |
| 222 | Fenpyroximate | 134098-61-6 | C24H27N3O4 | 19.75 | M + H | 422.20743 |
| 223 | Fensulfothion | 115-90-2 | C11H17O4PS2 | 12.87 | M + H | 309.03786 |
| 224 | Fensulfothion-oxon | 6552-21-2 | C11H17O5PS | 6.58 | M + H | 293.06071 |
| 225 | Fensulfothion-sulfone | 14255-72-2 | C11H17O5PS2 | 13.35 | M + H | 325.03278 |
| 226 | Fenthion | 55-38-9 | C10H15O3PS2 | 17.75 | M + H | 279.0273 |
| 227 | Fenthion oxon | 6552-12-1 | C10H15O4PS | 13.85 | M + H | 263.05014 |
| 228 | Fenthion oxon sulfone | 14086-35-2 | C10H15O6PS | 5.48 | M + H | 295.03997 |
| 229 | Fenthion oxon sulfoxide | 6552-13-2 | C10H15O5PS | 5.25 | M + H | 279.04506 |
| 230 | Fenthion sulfone | 3761-42-0 | C10H15O5PS2 | 10.39 | M + H | 311.01713 |
| 231 | Fenthion sulfoxide | 3761-41-9 | C10H15O4PS2 | 9.49 | M + H | 295.02221 |
| 232 | Fentrazamide | 158237-07-1 | C16H20ClN5O2 | 17.83 | M + Na | 372.11977 |
| 233 | Fenuron | 101-42-8 | C9H12N2O | 4.74 | M + H | 165.10224 |
| 234 | Flamprop | 58667-63-3 | C16H13ClFNO3 | 14.85 | M + H | 322.06408 |
| 235 | Flamprop-isopropyl | 52756-22-6 | C19H19ClFNO3 | 17.99 | M + H | 364.11103 |
| 236 | Flamprop-methyl | 52756-25-9 | C17H15ClFNO3 | 16.39 | M + H | 336.07973 |
| 237 | Flazasulfuron | 104040-78-0 | C13H12F3N5O5S | 13.81 | M + H | 408.0584 |
| 238 | Florasulam | 145701-23-1 | C12H8F3N5O3S | 6.2 | M + H | 360.03727 |
| 239 | Fluazifop | 69335-91-7 | C15H12F3NO4 | 15.16 | M + H | 328.07912 |
| 240 | Fluazifop-butyl | 69806-50-4 | C19H20F3NO4 | 18.98 | M + H | 384.14172 |
| 241 | Fluazifop-P-Butyl | 79241-46-6 | C19H20F3NO4 | 18.98 | M + H | 384.14172 |
| 242 | Flubendiamide | 272451-65-7 | C23H22F7IN2O4S | 17.82 | M + H | 683.03059 |

TABLE 2-continued

Over 500 pesticides list

| No. | Compound Name | CAS No. | ChemicalFormula | $t_R$ (min) | Adduct | Precursor |
|---|---|---|---|---|---|---|
| 243 | Flucarbazone | 145026-88-6 | C12H11F3N4O6S | 6.01 | M + H | 397.04242 |
| 244 | Flucycloxuron | 94050-52-9 | C25H20ClF2N3O3 | 19.46 | M + H | 484.1234 |
| 245 | Flufenacet | 142459-58-3 | C14H13F4N3O2S | 16.91 | M + H | 364.07374 |
| 246 | Flufenoxuron | 101463-69-8 | C21H11ClF6N2O3 | 19.56 | M + H | 489.04352 |
| 247 | Flufenpyr-ethyl | 188489-07-8 | C16H13ClF4N2O4 | 17.29 | M + NH4 | 426.08382 |
| 248 | Flumequine | 42835-25-6 | C14H12FNO3 | 9.51 | M + H | 262.0874 |
| 249 | Flumetsulam | 98967-40-9 | C12H9F2N5O2S | 4.68 | M + H | 326.05178 |
| 250 | Flumiclorac-pentyl | 87546-18-7 | C21H23ClFNO5 | 18.99 | M + H | 424.13216 |
| 251 | Flumorph | 211867-47-9 | C21H22FNO4 | 13.18 | M + H | 372.16056 |
| 252 | Fluometuron | 2164-17-2 | C10H11F3N2O | 10.11 | M + H | 233.08962 |
| 253 | Fluopicolide | 239110-15-7 | C14H8Cl3F3N2O | 15.74 | M + H | 382.97271 |
| 254 | Fluopyram | 658066-35-4 | C16H11ClF6N2O | 16.75 | M + H | 397.05369 |
| 255 | Fluoroglycofen-ethyl | 77501-90-7 | C18H13ClF3NO7 | 18.72 | M + H | 448.04054 |
| 256 | Fluoxastrobin | 361377-29-9 | C21H16ClFN4O5 | 16.82 | M + H | 459.0866 |
| 257 | Fluquinconazole | 136426-54-5 | C16H8Cl2FN5O | 16.39 | M + H | 376.01627 |
| 258 | Fluridone | 59756-60-4 | C19H14F3NO | 14.22 | M + H | 330.11003 |
| 259 | Flurochloridone | 61213-25-0 | C12H10Cl2F3NO | 16.17 | M + H | 312.01643 |
| 260 | Flurprimidol | 56425-91-3 | C15H15F3N2O2 | 15.93 | M + H | 313.11584 |
| 261 | Flurtamone | 96525-23-4 | C18H14F3NO2 | 15.07 | M + H | 334.10494 |
| 262 | Flusilazole | 85509-19-9 | C16H15F2N3Si | 17.45 | M + H | 316.10761 |
| 263 | Fluthiacet-Methyl | 117337-19-6 | C15H15ClFN3O3S2 | 17.52 | M + H | 404.03002 |
| 264 | Flutolanil | 66332-96-5 | C17H16F3NO2 | 15.88 | M + H | 324.12059 |
| 265 | Flutriafol | 76674-21-0 | C16H13F2N3O | 12.03 | M + H | 302.10995 |
| 266 | Fluxapyroxad | 907204-31-3 | C18H12F5N3O | 15.93 | M + H | 382.09733 |
| 267 | Fonofos | 944-22-9 | C10H15OPS2 | 17.8 | M + H | 247.03747 |
| 268 | Foramsulfuron | 173159-57-4 | C17H20N6O7S | 9.87 | M + H | 453.11869 |
| 269 | Forchlorfenuron | 68157-60-8 | C12H10ClN3O | 12.16 | M + H | 248.05852 |
| 270 | Fosthiazate | 98886-44-3 | C9H18NO3PS2 | 10.58 | M + H | 284.05385 |
| 271 | Fuberidazole | 3878-19-1 | C11H8N2O | 4.59 | M + H | 185.07094 |
| 272 | Furalaxyl | 57646-30-7 | C17H19NO4 | 14.88 | M + H | 302.13868 |
| 273 | Furathiocarb | 65907-30-4 | C18H26N2O5S | 18.94 | M + H | 383.16352 |
| 274 | Furmecyclox | 60568-05-0 | C14H21NO3 | 17.69 | M + H | 252.15942 |
| 275 | Halofenozide | 112226-61-6 | C18H19ClN2O2 | 15.11 | M + H | 331.12078 |
| 276 | Halosulfuron-methyl | 100784-20-1 | C13H15ClN6O7S | 16.26 | M + H | 435.04842 |
| 277 | Haloxyfop | 69806-34-4 | C15H11ClF3NO4 | 17.58 | M + H | 362.04015 |
| 278 | Haloxyfop-ehyoxyethyl | 87237-48-7 | C19H19ClF3NO5 | 18.91 | M + H | 434.09766 |
| 279 | Haloxyfop-methyl | 69806-40-2 | C16H13ClF3NO4 | 18.49 | M + H | 376.0558 |
| 280 | Heptenophos | 23560-59-0 | C9H12ClO4P | 13.01 | M + H | 251.02345 |
| 281 | Hexaconazole | 79983-71-4 | C14H17Cl2N3O | 17.99 | M + H | 314.08214 |
| 282 | Hexazinone | 51235-04-2 | C12H20N4O2 | 8.1 | M + H | 253.1659 |
| 283 | Hexythiazox | 78587-05-0 | C17H21ClN2O2S | 19.36 | M + H | 353.1085 |
| 284 | Hydramethylnon | 67485-29-4 | C25H24F6N4 | 18.72 | M + H | 495.19779 |
| 285 | Hymexazol | 10004-44-1 | C4H5NO2 | 2.42 | M + H | 100.0393 |
| 286 | Imazalil | 35554-44-0 | C14H14Cl2N2O | 11.36 | M + H | 297.0556 |
| 287 | Imazamethabenz-methyl | 81405-85-8 | C16H20N2O3 | 7.99 | M + H | 289.15467 |
| 288 | Imazamox | 114311-32-9 | C15H19N3O4 | 5.34 | M + H | 306.14483 |
| 289 | Imazapic | 104098-48-8 | C14H17N3O3 | 5.52 | M + H | 276.13427 |
| 290 | Imazapyr | 81334-34-1 | C13H15N3O3 | 4.37 | M + H | 262.11862 |
| 291 | Imazaquin | 81335-37-7 | C17H17N3O3 | 8.29 | M + H | 312.13427 |
| 292 | Imazethapyr | 81335-77-5 | C15H19N3O3 | 7 | M + H | 290.14992 |
| 293 | Imazosulfuron | 122548-33-8 | C14H13ClN6O5S | 15.33 | M + H | 413.04294 |
| 294 | Imibenconazole | 86598-92-7 | C17H13Cl3N4S | 19.15 | M + H | 410.99993 |
| 295 | Imidacloprid | 138261-41-3 | C9H10ClN5O2 | 4.46 | M + H | 256.05958 |
| 296 | Imidacloprid-urea | 120868-66-8 | C9H10ClN3O | 4.49 | M + H | 212.05852 |
| 297 | Inabenfide | 82211-24-3 | C19H15ClN2O2 | 14.54 | M + H | 339.08948 |
| 298 | Indoxacarb | 144171-61-9 | C22H17ClF3N3O7 | 18.61 | M + H | 528.07799 |
| 299 | Iodosulfuron-methyl | 185119-76-0 | C14H14IN5O6S | 13.82 | M + H | 507.97822 |
| 300 | Ipconazole | 125225-28-7 | C18H24ClN3O | 18.62 | M + H | 334.16807 |
| 301 | Iprobenfos | 26087-47-8 | C13H21O3PS | 17.59 | M + H | 289.10218 |
| 302 | Iprovalicarb | 140923-17-7 | C18H28N2O3 | 16.73 | M + H | 321.21727 |
| 303 | Isazofos | 42509-80-8 | C9H17ClN3O3PS | 16.35 | M + H | 314.04895 |
| 304 | Isocarbamid | 30979-48-7 | C8H15N3O2 | 5.62 | M + H | 186.1237 |
| 305 | Isocarbophos | 24353-61-5 | C8H8O4PS | 12.73 | M+ | 230.98754 |
| 306 | Isofenphos | 25311-71-1 | C15H24NO4PS | 18.24 | M+ | 245.00319 |
| 307 | Isofenphos oxon | 31120-85-1 | C15H24NO5P | 16.61 | M + H | 330.14649 |
| 308 | Isomethiozin | 57052-04-7 | C12H20N4OS | 17.51 | M + H | 269.14306 |
| 309 | Isoprocarb | 2631-40-5 | C11H15NO2 | 11.33 | M + H | 194.11756 |
| 310 | Isopropalin | 33820-53-0 | C15H23N3O4 | 19.94 | M + H | 310.17613 |
| 311 | Isoprothiolane | 50512-35-1 | C12H18O4S2 | 15.7 | M + H | 291.07193 |
| 312 | Isoproturon | 34123-59-6 | C12H18N2O | 12 | M + H | 207.14919 |
| 313 | Isouron | 55861-78-4 | C10H17N3O2 | 8.7 | M + H | 212.13935 |
| 314 | Isoxaben | 82558-50-7 | C18H24N2O4 | 15.86 | M + H | 333.18088 |
| 315 | Isoxadifen-ethyl | 163520-33-0 | C18H17NO3 | 17.5 | M + H | 296.12812 |
| 316 | Isoxaflutole | 141112-29-0 | C15H12F3NO4S | 12.75 | M + H | 360.05119 |
| 317 | Isoxathion | 18854-01-8 | C13H16NO4PS | 18.21 | M + H | 314.06104 |
| 318 | Ivermectin | 70288-86-7 | C48H74O14 | 20.75 | M + NH4 | 892.54168 |

TABLE 2-continued

Over 500 pesticides list

| No. | Compound Name | CAS No. | ChemicalFormula | $t_R$ (min) | Adduct | Precursor |
|---|---|---|---|---|---|---|
| 319 | Kadethrin | 58769-20-3 | C23H24O4S | 18.72 | M + H | 397.14681 |
| 320 | Karbutilate | 4849-32-5 | C14H21N3O3 | 8.26 | M + H | 280.16557 |
| 321 | Kresoxim-methyl | 143390-89-0 | C18H19NO4 | 17.53 | M + H | 314.13868 |
| 322 | Lactofen | 77501-63-4 | C19H15ClF3NO7 | 19.08 | M + NH4 | 479.08274 |
| 323 | Linuron | 330-55-2 | C9H10Cl2N2O2 | 14.32 | M + H | 249.01921 |
| 324 | Malaoxon | 1634-78-2 | C10H19O7PS | 8.76 | M + H | 315.06619 |
| 325 | Malathion | 121-75-5 | C10H19O6PS2 | 15.76 | M + H | 331.04334 |
| 326 | Mandipropamid | 374726-62-2 | C23H22ClNO4 | 15.96 | M + H | 412.13101 |
| 327 | Mecarbam | 2595-54-2 | C10H20NO5PS2 | 16.71 | M + H | 330.05933 |
| 328 | Mefenacet | 73250-68-7 | C16H14N2O2S | 16.21 | M + H | 299.08487 |
| 329 | Mefenpyr-diethyl | 135590-91-9 | C16H18Cl2N2O4 | 18 | M + H | 373.07164 |
| 330 | Mepanipyrim | 110235-47-7 | C14H13N3 | 16.5 | M + H | 224.11822 |
| 331 | Mephosfolan | 950-10-7 | C8H16NO3PS2 | 7.93 | M + H | 270.0382 |
| 332 | Mepiquat chloride | 15302-91-7 | C7H16N | 0.8 | M+ | 114.12773 |
| 333 | Mepronil | 55814-41-0 | C17H19NO2 | 15.65 | M + H | 270.14886 |
| 334 | Mesosuifuron-methyl | 208465-21-8 | C17H21N5O9S2 | 12.34 | M + H | 504.08535 |
| 335 | Metalaxyl | 57837-19-1 | C15H21NO4 | 12.48 | M + H | 280.15433 |
| 336 | Metalaxyl-M | 70630-17-0 | C15H21NO4 | 12.48 | M + H | 280.15433 |
| 337 | Metamitron | 41394-05-2 | C10H10N4O | 4.77 | M + H | 203.09274 |
| 338 | Desamino-metamitron | 36993-94-9 | C10H9N3O | 4.66 | M + H | 188.08184 |
| 339 | Metazachlor | 67129-08-2 | C14H16ClN3O | 12.11 | M + H | 278.10547 |
| 340 | Metconazole | 125116-23-6 | C17H22ClN3O | 18.06 | M + H | 320.15242 |
| 341 | Methabenzthiazuron | 18691-97-9 | C10H11N3OS | 11.84 | M + H | 222.06956 |
| 342 | Methamidophos | 10265-92-6 | C2H8NO2PS | 2 | M + H | 142.00861 |
| 343 | Methidathion | 950-37-8 | C6H11N2O4PS3 | 12.8 | M + H | 302.96913 |
| 344 | Methiocarb | 2032-65-7 | C11H15NO2S | 14.6 | M + H | 226.08963 |
| 345 | Methiocarb Sulfone | 2179-25-1 | C11H15NO4S | 5.32 | M + NH4 | 275.106 |
| 346 | Methiocarb sulfoxide | 2635-10-1 | C11H15NO3S | 4.81 | M + H | 242.08454 |
| 347 | Methomyl | 16752-77-5 | C5H10N2O2S | 3.63 | M + H | 163.05357 |
| 348 | Methoprotryne | 841-06-5 | C11H21N5OS | 12.35 | M + H | 272.15396 |
| 349 | Methoxyfenozide | 161050-58-4 | C22H28N2O3 | 16.29 | M + H | 369.21727 |
| 350 | Metobromuron | 3060-89-7 | C9H11BrN2O2 | 10.93 | M + H | 259.00767 |
| 351 | Metolachlor | 51218-45-2 | C15H22ClNO2 | 16.91 | M + H | 284.14118 |
| 352 | Metolcarb | 1129-41-5 | C9H11NO2 | 6.94 | M + H | 166.08626 |
| 353 | Metominostrobin-(E) | 133408-50-1 | C16H16N2O3 | 13.18 | M + H | 285.12337 |
| 354 | Metominostrobin-(Z) | 133408-51-2 | C16H16N2O3 | 13.18 | M + H | 285.12337 |
| 355 | Metosulam | 139528-85-1 | C14H13Cl2N5O4S | 9.29 | M + H | 418.01381 |
| 356 | Metoxuron | 19937-59-8 | C10H13ClN2O2 | 6.46 | M + H | 229.07383 |
| 357 | Metrafenone | 220899-03-6 | C19H21BrO5 | 18.25 | M + H | 409.06451 |
| 358 | Metribuzin | 21087-64-9 | C8H14N4OS | 7.38 | M + H | 215.09611 |
| 359 | Metsulfuron-methyl | 74223-64-6 | C14H15N5O6S | 8.45 | M + H | 382.08158 |
| 360 | Mevinphos | 7786-34-7 | C7H13O6P | 5.86 | M + H | 225.05225 |
| 361 | Mexacarbate | 315-18-4 | C12H18N2O2 | 4.69 | M + H | 223.1441 |
| 362 | Molinate | 2212-67-1 | C9H17NOS | 15.48 | M + H | 188.11036 |
| 363 | Monocrotophos | 6923-22-4 | C7H14NO5P | 4.02 | M + H | 224.06824 |
| 364 | Monolinuron | 1746-81-2 | C9H11ClN2O2 | 9.56 | M + H | 215.05818 |
| 365 | Monuron | 150-68-5 | C9H11ClN2O | 7.48 | M + H | 199.06327 |
| 366 | Myclobutanil | 88671-89-0 | C15H17ClN4 | 16.17 | M + H | 289.12145 |
| 367 | Naproanilide | 52570-16-8 | C19H17NO2 | 17.35 | M + H | 292.13321 |
| 368 | Napropamide | 15299-99-7 | C17H21NO2 | 16.91 | M + H | 272.16451 |
| 369 | Naptalam | 132-66-1 | C18H13NO3 | 8.41 | M + H | 292.09682 |
| 370 | Neburon | 555-37-3 | C12H16Cl2N2O | 17.41 | M + H | 275.07125 |
| 371 | Nicosulfuron | 111991-09-4 | C15H18N6O6S | 7.87 | M + H | 411.10813 |
| 372 | Nitenpyram | 120738-89-8 | C11H15ClN4O2 | 3.41 | M + H | 271.09563 |
| 373 | Nitralin | 4726-14-1 | C13H19N3O6S | 17.2 | M + H | 346.10673 |
| 374 | Norflurazon | 27314-13-2 | C12H9ClF3N3O | 12.57 | M + H | 304.0459 |
| 375 | Nuarimol | 63284-71-9 | C17H12ClFN2O | 14.77 | M + H | 315.0695 |
| 376 | Octhilinone | 26530-20-1 | C11H19NOS | 17.02 | M + H | 214.12601 |
| 377 | Ofurace | 58810-48-3 | C14H16ClNO3 | 8.28 | M + H | 282.08915 |
| 378 | Omethoate | 1113-02-6 | C5H12NO4PS | 2.81 | M + H | 214.02974 |
| 379 | Orbencarb | 34622-58-7 | C12H16ClNOS | 18.09 | M + H | 258.07139 |
| 380 | Orthosulfamuron | 213464-77-8 | C16H20N6O6S | 12.78 | M + H | 425.12378 |
| 381 | Oxadixyl | 77732-09-3 | C14H18N2O4 | 7.04 | M + H | 279.13393 |
| 382 | Oxamyl | 23135-22-0 | C7H13N3O3S | 3.42 | M + NH4 | 237.10159 |
| 383 | Oxamyl-oxime | 30558-43-1 | C5H10N2O2S | 2.73 | M + H | 163.05357 |
| 384 | Oxaziclomefone | 153197-14-9 | C20H19Cl2NO2 | 18.92 | M + H | 376.08656 |
| 385 | Oxine-Copper | 10380-28-6 | C18H12CuN2O2 | 6.89 | M + H | 352.02676 |
| 386 | Oxycarboxin | 5259-88-1 | C12H13NO4S | 5.36 | M + H | 268.06381 |
| 387 | Paclobutrazol | 76738-62-0 | C15H20ClN3O | 15.6 | M + H | 294.13677 |
| 388 | Paraoxon-ethyl | 311-45-5 | C10H14NO6P | 11.7 | M + H | 276.06315 |
| 389 | Paraoxon-methyl | 950-35-6 | C8H10NO6P | 6.78 | M + H | 248.03185 |
| 390 | Pebulate | 1114-71-2 | C10H21NOS | 18.32 | M + H | 204.14166 |
| 391 | Penconazole | 66246-88-6 | C13H15Cl2N3 | 17.69 | M + H | 284.07158 |
| 392 | Pencycuron | 66063-05-6 | C19H21ClN2O | 18.36 | M + H | 329.14152 |
| 393 | Pendimethalin | 40487-42-1 | C13H19N3O4 | 19.45 | M + H | 282.14483 |
| 394 | Penoxsulam | 219714-96-2 | C16H14F5N5O5S | 10.99 | M + H | 484.07086 |

TABLE 2-continued

Over 500 pesticides list

| No. | Compound Name | CAS No. | ChemicalFormula | $t_R$ (min) | Adduct | Precursor |
|---|---|---|---|---|---|---|
| 395 | Pentanochlor | 2307-68-8 | C13H18ClNO | 17.31 | M + H | 240.11497 |
| 396 | Phenmedipham | 13684-63-4 | C16H16N2O4 | 13.82 | M + NH4 | 318.14483 |
| 397 | Phenthoate | 2597-3-7 | C12H17O4PS2 | 17.56 | M + H | 321.03786 |
| 398 | Phorate | 298-02-2 | C7H17O2PS3 | 18.08 | M + H | 261.0201 |
| 399 | Phorate-oxon-sulfone | 2588-6-9 | C7H17O5PS2 | 5.49 | M + H | 277.03278 |
| 400 | Phorate-Sulfone | 2588-4-7 | C7H17O4PS3 | 11.47 | M + H | 293.00993 |
| 401 | Phorate-Sulfoxide | 2588-3-6 | C7H17O3PS3 | 10.95 | M + H | 277.01502 |
| 402 | Phosalone | 2310-17-0 | C12H15ClNO4PS2 | 18.2 | M + H | 367.99414 |
| 403 | Phosfolan | 947-02-4 | C7H14NO3PS2 | 6.39 | M + H | 256.02255 |
| 404 | Phosmet | 732-11-6 | C11H12NO4PS2 | 13.85 | M + H | 318.00181 |
| 405 | Phosmet oxon | 3735-33-9 | C11H12NO5PS | 6.88 | M + H | 302.02466 |
| 406 | Phosphamidon | 13171-21-6 | C10H19ClNO5P | 7.33 | M + H | 300.07621 |
| 407 | Phoxim | 14816-18-3 | C12H15N2O3PS | 18.14 | M + H | 299.06138 |
| 408 | Phthalic acid, benzyl butyl ester | 85-68-7 | C19H20O4 | 18.64 | M + H | 313.14344 |
| 409 | Phthalic acid, dicyclohexyl ester | 84-61-7 | C20H26O4 | 19.67 | M + H | 331.19039 |
| 410 | Phthalic acid, bis-butyl | 84-74-2 | C16H22O4 | 18.66 | M + H | 279.15909 |
| 411 | Picaridin | 119515-38-7 | C12H23NO3 | 13.76 | M + H | 230.17507 |
| 412 | Picloram | 1918-02-1 | C6H3Cl3N2O2 | 3.23 | M + H | 240.93329 |
| 413 | Picolinafen | 137641-05-5 | C19H12F4N2O2 | 19.22 | M + H | 377.09077 |
| 414 | Picoxystrobin | 117428-22-5 | C18H16F3NO4 | 17.54 | M + H | 368.11042 |
| 415 | Pinoxaden | 2.43973-20-8 | C23H32N2O4 | 18.28 | M + H | 401.24348 |
| 416 | Piperonyl Butoxide | 51-03-6 | C19H30O5 | 19.12 | M + NH4 | 356.24315 |
| 417 | Piperophos | 24151-93-7 | C14H28NO3PS2 | 18.54 | M + H | 354.1321 |
| 418 | Pirimicarb | 23103-98-2 | C11H18N4O2 | 6.34 | M + H | 239.15025 |
| 419 | Pirimicarb-desmethyl-formamido | 27218-04-8 | C11H16N4O3 | 7.86 | M + H | 253.12952 |
| 420 | Pirimiphos-ethyl | 23505-41-1 | C13H24N3O3PS | 18.97 | M + H | 334.13488 |
| 421 | Pirimiphos-methyl | 29232-93-7 | C11H20N3O3PS | 17.84 | M + H | 306.10358 |
| 422 | Pirimiphos-methyl-N-desethyl | 67018-59-1 | C9H16N3O3PS | 11.53 | M + H | 278.07228 |
| 423 | Prallethrin | 23031-36-9 | C19H24O3 | 18.51 | M + H | 301.17982 |
| 424 | Pretilachlor | 51218-49-6 | C17H26ClNO2 | 18.66 | M + H | 312.17248 |
| 425 | Primisulfuron-methyl | 86209-51-0 | C15H12F4N4O7S | 16.31 | M + H | 469.04356 |
| 426 | Prochloraz | 67747-09-5 | C15H16Cl3N3O2 | 17.87 | M + H | 376.03809 |
| 427 | Profenofos | 41198-08-7 | C11H15BrClO3PS | 18.89 | M + H | 372.94242 |
| 428 | Promecarb | 2631-37-0 | C12H17NO2 | 15.21 | M + H | 208.13321 |
| 429 | Prometon | 1610-18-0 | C10H19N5O | 9.48 | M + H | 226.16624 |
| 430 | Prometryne | 7287-19-6 | C10H19N5S | 14.6 | M + H | 242.14339 |
| 431 | Pronamide | 23950-58-5 | C12H11Cl2NO | 15.13 | M + H | 256.02905 |
| 432 | Propachlor | 1918-16-7 | C11H14ClNO | 12.03 | M + H | 212.08367 |
| 433 | Propamocarb | 24579-73-5 | C9H20N2O2 | 2.85 | M + H | 189.15975 |
| 434 | Propanil | 709-98-8 | C9H9Cl2NO | 14.22 | M + H | 218.0134 |
| 435 | Propaphos | 7292-16-2 | C13H21O4PS | 17.79 | M + H | 305.09709 |
| 436 | Propaquizafop | 111479-05-1 | C22H22ClN3O5 | 19.04 | M + H | 444.13207 |
| 437 | Propargite | 2312-35-8 | C19H26O4S | 19.52 | M + NH4 | 368.18901 |
| 438 | Propazine | 139-40-2 | C9H16ClN5 | 14.18 | M + H | 230.1167 |
| 439 | Propetamphos | 31218-83-4 | C10H20NO4PS | 16.19 | M + H | 282.09234 |
| 440 | Propiconazole | 60207-90-1 | C15H17Cl2N3O2 | 17.97 | M + H | 342.07706 |
| 441 | Propisochlor | 86763-47-5 | C15H22ClNO2 | 17.69 | M + H | 284.14118 |
| 442 | Propoxur | 114-26-1 | C11H15NO3 | 7.85 | M + H | 210.11247 |
| 443 | Propoxycarbazone | 145026-81-9 | C15H18N4O7S | 7.4 | M + NH4 | 416.12345 |
| 444 | Proquinazid | 189278-12-4 | C14H17IN2O2 | 19.9 | M + H | 373.04075 |
| 445 | Prosulfocarb | 52888-80-9 | C14H21NOS | 18.75 | M + H | 252.14166 |
| 446 | Prothioconazole | 178928-70-6 | C14H15Cl2N3OS | 17.78 | M + H | 344.03856 |
| 447 | Prothoate | 2275-18-5 | C9H20NO3PS2 | 17.68 | M + H | 286.0695 |
| 448 | Pymetrozine | 123312-89-0 | C10H11N5O | 2.87 | M + H | 218.10364 |
| 449 | Pyraclofos | 89784-60-1 | C14H18ClN2O3PS | 18.2 | M + H | 361.0537 |
| 450 | Pyraclostrobin | 175013-18-0 | C19H18ClN3O4 | 18.12 | M + I-I | 388.10586 |
| 451 | Pyraflufen | 129630-17-7 | C13H9Cl2F3N2O4 | 15.25 | M + H | 384.99642 |
| 452 | Pyraflufen-ethyl | 129630-19-9 | C15H13Cl2F3N2O4 | 17.94 | M + H | 413.02772 |
| 453 | Pyrasulfotole | 365400-11-9 | C14H13F3N2O4S | 6.6 | M + H | 363.06209 |
| 454 | Pyrazolynate | 58011-68-0 | C19H16Cl2N2O4S | 18.35 | M + H | 439.02806 |
| 455 | Pyrazophos | 13457-18-6 | C14H20N3O5PS | 18.13 | M + H | 374.0934 |
| 456 | Pyrazosulfuron-ethyl | 93697-74-6 | C14H18N6O7S | 16.25 | M + H | 415.10304 |
| 457 | Pyrazoxyfen | 71561-11-0 | C20H16Cl2N2O3 | 17.82 | M + H | 403.06107 |
| 458 | Pyributicarb | 88678-67-5 | C18H22N2O2S | 19.24 | M + H | 331.14748 |
| 459 | Pyridaben | 96489-71-3 | C19H25ClN2OS | 20.05 | M + H | 365.14489 |
| 460 | Pyridalyl | 179101-81-6 | C18H14Cl4F3NO3 | 21.15 | M + H | 489.97527 |
| 461 | Pyridaphenthion | 119-12-0 | C14H17N2O4PS | 16.34 | M + H | 341.07194 |
| 462 | Pyridate | 55512-33-9 | C19H23ClN2O2S | 20.4 | M + H | 379.12415 |
| 463 | Pyrifenox | 88283-41-4 | C14H12Cl2N2O | 14.62 | M + H | 295.03994 |
| 464 | Pyriftalid | 135186-78-6 | C15H14N2O4S | 14 | M + H | 319.0747 |
| 465 | Pyrimethanil | 53112-28-0 | C12H13N3 | 12.79 | M + H | 200.11822 |
| 466 | Pyrimidifen | 105779-78-0 | C20H28ClN3O2 | 18.89 | M + H | 378.19428 |
| 467 | Pyriminobac-methyl(z) | 147411-70-9 | C17H19N3O6 | 14.19 | M + H | 362.13466 |
| 468 | Pyrimitate | 5221-49-8 | C11H20N3O3PS | 0 | M + H | 306.10358 |
| 469 | Pyriproxyfen | 95737-68-1 | C20H19NO3 | 19.26 | M + H | 322.14377 |
| 470 | Pyroquilon | 57369-32-1 | C11H11NO | 8 | M + H | 174.09134 |

TABLE 2-continued

Over 500 pesticides list

| No. | Compound Name | CAS No. | ChemicalFormula | $t_R$ (min) | Adduct | Precursor |
|---|---|---|---|---|---|---|
| 471 | Quinalphos | 13593-03-8 | C12H15N2O3PS | 17.47 | M + H | 299.06138 |
| 472 | Quinclorac | 84087-01-4 | C10H5Cl2NO2 | 5.91 | M + H | 241.97701 |
| 473 | Quinmerac | 90717-03-6 | C11H8ClNO2 | 4.82 | M + H | 222.03163 |
| 474 | Quinoclamine | 2797-51-5 | C10H6ClNO2 | 7.33 | M + H | 208.01598 |
| 475 | Quinoxyfen | 124495-18-7 | C15H8Cl2FNO | 19.46 | M + H | 308.00397 |
| 476 | Quizalofop | 76578-12-6 | C17H13ClN2O4 | 17.16 | M + H | 345.06366 |
| 477 | Quizalofop-ethyl | 76578-14-8 | C19H17ClN2O4 | 18.85 | M + H | 373.09496 |
| 478 | Quizalofop-P-Ethyl | 100646-51-3 | C19H17ClN2O4 | 18.86 | M + H | 373.09496 |
| 479 | Rabenzazole | 40341-04-6 | C12H12N4 | 11.47 | M + H | 213.11347 |
| 480 | Resmethrin | 10453-86-8 | C22H26O3 | 20.22 | M + H | 339.19547 |
| 481 | RF 5849 | 112225-87-3 | C18H20N2O2 | 10.97 | M + H | 297.15975 |
| 482 | Rimsulfuron | 122931-48-0 | C14H17N5O7S2 | 9.72 | M + Na | 454.04616 |
| 483 | Rotenone | 83-79-4 | C23H22O6 | 17.28 | M + H | 395.14891 |
| 484 | Saflufenacil | 372137-35-4 | C17H17ClF4N4O5S | 14.58 | M + NH4 | 518.08826 |
| 485 | Sebutylazine | 7286-69-3 | C9H16ClN5 | 13.94 | M + H | 230.1167 |
| 486 | Secbumeton | 26259-45-0 | C10H19N5O | 9.76 | M + H | 226.16624 |
| 487 | Sethoxydim | 74051-80-2 | C17H29NO3S | 0 | M + H | 328.19409 |
| 488 | Siduron | 1982-49-6 | C14H20N2O | 14.48 | M + H | 233.16484 |
| 489 | Simazine | 122-34-9 | C7H12ClN5 | 7.8 | M + H | 202.0854 |
| 490 | Simeconazole | 149508-90-7 | C14H20FN3OSi | 16.87 | M + H | 294.14324 |
| 491 | Simeton | 673-04-1 | C8H15N5O | 5.39 | M + H | 198.13494 |
| 492 | Simetryn | 1014-70-6 | C8H15N5S | 7.94 | M + H | 214.11209 |
| 493 | S-Metolachlor | 87392-12-9 | C15H22ClNO2 | 16.93 | M + H | 284.14118 |
| 494 | Spinetoram | 187166-40-1 | C42H69NO10 | 18.72 | M + H | 748.49942 |
| 495 | Spinosad | 168316-95-8 | C41H65NO10 | 18.28 | M + H | 732.46812 |
| 496 | Spirodiclofen | 148477-71-8 | C21H24Cl2O4 | 19.79 | M + H | 411.11244 |
| 497 | Spirotetramat | 203313-25-1 | C21H27NO5 | 16.78 | M + H | 374.1962 |
| 498 | Spiroxamine | 118134-30-8 | C18H35NO2 | 15.28 | M + H | 298.27406 |
| 499 | Sulcotrione | 99105-77-8 | C14H13ClO5S | 7.33 | M + H | 329.0245 |
| 500 | Sulfallate | 95-06-7 | C8H14ClNS2 | 17.55 | M + H | 224.0329 |
| 501 | Sulfentrazone | 122836-35-5 | C11H10Cl2F2N4O3S | 8.96 | M + H | 386.98915 |
| 502 | Sulfotep | 3689-24-5 | C8H20O5P2S2 | 17.73 | M + H | 323.03001 |
| 503 | Sulfoxaflor | 946578-00-3 | C10H10F3N3OS | 5.18 | M + H | 278.05694 |
| 504 | Sulprofos | 35400-43-2 | C12H19O2PS3 | 19.47 | M + H | 323.03576 |
| 505 | Tebuconazole | 107534-96-3 | C16H22ClN3O | 17.69 | M + H | 308.15242 |
| 506 | Tebufenozide | 112410-23-8 | C22H28N2O2 | 17.54 | M + H | 353.22235 |
| 507 | Tebufenpyrad | 119168-77-3 | C18H24ClN3O | 19.03 | M + H | 334.16807 |
| 508 | Tebupirimfos | 96182-53-5 | C13H23N2O3PS | 19.09 | M + H | 319.12398 |
| 509 | Tebutam | 35256-85-0 | C15H23NO | 16.99 | M + H | 234.18524 |
| 510 | Tebuthiuron | 34014-18-1 | C9H16N4OS | 8.35 | M + H | 229.11176 |
| 511 | Tembotrione | 335104-84-2 | C17H16ClF3O6S | 14.12 | M + NH4 | 458.06465 |
| 512 | Temephos | 3383-96-8 | C16H20O6P2S3 | 19.15 | M + H | 466.997 |
| 513 | Tepraloxydim | 149979-41-9 | C17H24ClNO4 | 16.47 | M + H | 342.14666 |
| 514 | Terbucarb | 1918-11-2 | C17H27NO2 | 18.53 | M + H | 278.21146 |
| 515 | Terbufos | 13071-79-9 | C9H21O2PS3 | 19 | M + H | 289.05141 |
| 516 | Terbufos sulfone | 56070-16-7 | C9H21O4PS3 | 14.37 | M + H | 321.04123 |
| 517 | Terbufos-O-analogue sulfone | 56070-15-6 | C9H21O5PS2 | 7.14 | M + H | 305.06408 |
| 518 | Terbumeton | 33693-04-8 | C10H19N5O | 9.95 | M + H | 226.16624 |
| 519 | Terbuthylazine | 5915-41-3 | C9H16ClN5 | 14.88 | M + H | 230.1167 |
| 520 | Terbutryne | 886-50-0 | C10H19N5S | 14.71 | M + H | 242.14339 |
| 521 | Tetrachlorvinphos | 22248-79-9 | C10H9Cl4O4P | 17.44 | M + H | 364.90653 |
| 522 | Tetraconazole | 112281-77-3 | C13H11Cl2F4N3O | 17.05 | M + H | 372.02881 |
| 523 | Tetramethrin | 7696-12-0 | C19H25NO4 | 18.95 | M + H | 332.18563 |
| 524 | Thenylchlor | 96491-05-3 | C16H18ClNO2S | 16.82 | M + H | 324.08195 |
| 525 | Thiabendazole | 148-79-8 | C10H7N3S | 4.47 | M + H | 202.04334 |
| 526 | Thiabendazole-5-hydroxy | 948-71-0 | C10H7N3OS | 3.68 | M + H | 218.03826 |
| 527 | Thiacloprid | 111988-49-9 | C10H9ClN4S | 5.8 | M + H | 253.03092 |
| 528 | Thiamethoxam | 153719-23-4 | C8H10ClN5O3S | 3.79 | M + H | 292.02656 |
| 529 | Thiazafluron | 25366-23-8 | C6H7F3N4OS | 8.01 | M + H | 241.03654 |
| 530 | Thiazopyr | 117718-60-2 | C16H17F5N2O2S | 17.82 | M + H | 397.10037 |
| 531 | Thidiazuron | 51707-55-2 | C9H8N4OS | 7.72 | M + H | 221.04916 |
| 532 | Thiencarbazone-methyl | 317815-83-1 | C12H14N4O7S2 | 6.91 | M + H | 391.03767 |
| 533 | Thifensulfuron-methyl | 79277-27-3 | C12H13N5O6S2 | 7.86 | M + H | 388.038 |
| 534 | Thiobencarb | 28249-77-6 | C12H16ClNOS | 18.28 | M + H | 258.07139 |
| 535 | Thiocyclam | 31895-21-3 | C5H11NS3 | 2.2 | M + H | 182.01264 |
| 536 | Thiodicarb | 59669-26-0 | C10H18N4O4S3 | 11.25 | M + H | 355.05629 |
| 537 | Thiofanox | 39196-18-4 | C9H18N2O2S | 9.96 | M + H | 219.11618 |
| 538 | Thiofanox sulfone | 39184-59-3 | C9H18N2O4S | 4.68 | M + H | 251.106 |
| 539 | Thiofanox-Sulfoxide | 39184-27-5 | C9H18N2O3S | 4.46 | M + H | 235.11109 |
| 540 | Thionazin | 297-97-2 | C8H13N2O3PS | 11.98 | M + H | 249.04573 |
| 541 | Thiophanate-Ethyl | 23564-06-9 | C14H18N4O4S2 | 12.75 | M + H | 371.08422 |
| 542 | Thiophanate-methyl | 23564-05-8 | C12H14N4O4S2 | 7.67 | M + H | 343.05292 |
| 543 | Thiram | 137-26-8 | C6H12N2S4 | 7.44 | M + H | 240.99561 |
| 544 | Tiocarbazil | 36756-79-3 | C16H25NOS | 19.58 | M + H | 280.17296 |
| 545 | Tolclofos-methyl | 57018-04-9 | C9H11Cl2O3PS | 18.24 | M + H | 300.96163 |
| 546 | Tolfenpyrad | 129558-76-5 | C21H22ClN3O2 | 19.15 | M + H | 384.14733 |

TABLE 2-continued

Over 500 pesticides list

| No. | Compound Name | CAS No. | ChemicalFormula | $t_R$ (min) | Adduct | Precursor |
|---|---|---|---|---|---|---|
| 547 | Tralkoxydim | 87820-88-0 | C20H27NO3 | 19.33 | M + H | 330.20637 |
| 548 | Triadimefon | 43121-43-3 | C14H16ClN3O2 | 15.96 | M + H | 294.10038 |
| 549 | Triadimenol | 55219-65-3 | C14H18ClN3O2 | 16.35 | M + H | 296.11603 |
| 550 | Tri-allate | 2303-17-5 | C10H16Cl3NOS | 19.46 | M + H | 304.00909 |
| 551 | Triapenthenol | 76608-88-3 | C15H25N3O | 17.35 | M + H | 264.20704 |
| 552 | Triasulfuron | 82097-50-5 | C14H16ClN5O5S | 8.07 | M + H | 402.06334 |
| 553 | Triazophos | 24017-47-8 | C12H16N3O3PS | 16.46 | M + H | 314.07228 |
| 554 | Triazoxide | 72459-58-6 | C10H6ClN5O | 10.72 | M + H | 248.03336 |
| 555 | Tribenuron-methyl | 101200-48-0 | C15H17N5O6S | 17.11 | M + H | 396.09723 |
| 556 | Tribufos | 78-48-8 | C12H27OPS3 | 20.02 | M + H | 315.10344 |
| 557 | Trichlorfon | 52-68-6 | C4H8Cl3O4P | 4.69 | M + H | 256.92985 |
| 558 | Tricyclazole | 41814-78-2 | C9H7N3S | 6.6 | M + H | 190.04334 |
| 559 | Tridemorph | 81412-43-3 | C19H39NO | 17.9 | M + H | 298.31044 |
| 560 | Trietazine | 1912-26-1 | C9H16ClN5 | 16.26 | M + H | 230.1167 |
| 561 | Trifloxystrobin | 141517-21-7 | C20H19F3N2O4 | 18.63 | M + H | 409.13697 |
| 562 | Triflumizole | 99387-89-0 | C15H15ClF3N3O | 18.64 | M + H | 346.09285 |
| 563 | Triflumuron | 64628-44-0 | C15H10ClF3N2O3 | 18.17 | M + H | 359.04048 |
| 564 | Triflusulfuron-methyl | 126535-15-7 | C17H19F3N6O6S | 15.85 | M + H | 493.11116 |
| 565 | Tri-n-butyl phosphate | 126-73-8 | C12H27O4P | 18.71 | M + H | 267.17197 |
| 566 | Trinexapac-ethyl | 95266-40-3 | C13H16O5 | 12.41 | M + H | 253.10705 |
| 567 | Triphenyl-phosphate | 603-35-0 | C18H15O4P | 18.07 | M + H | 327.07807 |
| 568 | Triticonazole | 131983-72-7 | C17H20ClN3O | 16.68 | M + H | 318.13677 |
| 569 | Uniconazole | 83657-22-1 | C15H18ClN3O | 17.22 | M + H | 292.12112 |
| 570 | Validamycin | 37248-47-8 | C20H35NO13 | 0.75 | M + H | 498.21812 |
| 571 | Valifenalate | 283159-90-0 | C19H27ClN2O5 | 16.68 | M + H | 399.16813 |
| 572 | Vamidothion | 2275-23-2 | C8H18NO4PS2 | 4.91 | M + H | 288.04876 |
| 573 | Vamidothion sulfone | 70898-34-9 | C8H18NO6PS2 | 3.78 | M + H | 320.03859 |
| 574 | Vamidothion sulfoxide | 20300-00-9 | C8H18NO5PS2 | 3.43 | M + H | 304.04368 |
| 575 | Zoxamide | 156052-68-5 | C14H16Cl3NO2 | 17.76 | M + H | 336.03194 |

Example 1

Example of LC-Q-Orbitrap screening and confirmation techniques for over 500 pesticide (as described above) in market apple.

1). The specific steps of sample pretreatment:

1.1 The edible portion of the apple samples is chopped, blended, sealed, and labelled.

1.2 Weigh 10.0 g. (accurate to 0.01 g) of sample to 100 mL centrifuge tube, add 40 mL of 1% acetonitrile acetic acid to extract, and the mixture was then blended by homogenizer at 10 000 rpm for 1 min, add anhydrous magnesium sulfate and sodium chloride (mass ratio, 4/1), the centrifuge tube was shaken for 10 min, and then centrifuged at 4200 rpm for 5 min, take 20 mL of supernatants into 150 mL heart-shaped bottle, and evaporate to 1 mL on a rotary evaporator at 40° C. water bath for clean-up.

1.3 Add anhydrous sodium sulfate for a height of about 2 cm into SPE column, SPE purification column was pre-washed with 5 mL of acetonitrile-toluene, tap purification column gently to remove bubble and discard the effluent under the purification column, when the liquid level is slightly above the top of sodium sulfate, transfer the sample concentrate into SPE column and put a 50 mL heart-shaped bottle below it to receive them, wash the heart-shaped bottle 2 times with 2 mL of acetonitrile-toluene each time and transfer the cleansing fluid into purification column. A 20 mL reservoir was connected to the column, elute with 25 mL of acetonitrile-toluene, collected and evaporated to 0.5 mL on a rotary evaporator 1.4 Blow the concentrated solutions with nitrogen till dryness, add 1 mL of acetonitrile-water solution and ultrasonic dissolved, and filtered through a 0.22 μm nylon membrane for LC-Q-Orbitrap analysis.

2). LC-Q-Orbitrap operation conditions

Separation through liquid chromatography system, which is equipped with reversed phase column (Accucore aQ 150×2.1 mm, 2.6 μm); mobile phase solution A: 5 mM ammonium acetate-0.1% formic acid-water; mobile phase solution B: 0.1% formic acid-methanol; gradient elution program: 0 min: 1% B, 3 min: 30% B, 6 min: 40% B, 9 min: 40% B, 15 min: 60% B, 19 min: 90% B, 23 min: 90% B, 23.01 min: 1% B, post run for 4 min flow rate: 0.4 mL/min; column temperature: 40° C.; injection volume: 5 μL.

Mass spectrometry conditions: scan mode: Full MS/dd-MS$^2$; Full MS mass scan range: 70-1050 m/z; Resolution: 70,000, Full MS; 17,500, MS/MS; AGC: Full MS, 1e6; MS/MS, 1e5; Max IT: Full MS, 200 ms; MS/MS, 60 ms; Loop count: 1; MSX count: 1; Isolation width: 2.0 m/z; NCE (Stepped NCE): 40 (50%); Under fill ratio: 1%; Apex trigger: 2-6 s; Dynamic Exclusion: 5 s; the mass spectrometry results is collected and processed by software TraceFinder.

3). Extract the retention time and the accurate mass number of corresponding adduct ions in the chromatogram in order, and make a retrieval in the electronic ID databases while recording the electronic ID information of the retention time and the accurate mass number of corresponding adduct ions. The mass spectrum is obtained by bombarding with the corresponding collision energy in the database, and an electronic ID of suspected pesticides of the apple sample corresponding to all retention times is established.

4). The electronic ID of suspected pesticides of the apple sample is sequentially compared with those electronic ID of pesticide compound in the database. If $\Delta T \leq 0.3$ and $\Delta P \leq 10\%$, recording that pesticide, otherwise comparing the next suspected pesticide electronic ID.

5). After detection is completed, the information of the pesticide contained in the apple sample solution will be displayed.

LC-Q-Orbitrap screening results in apple samples from a provincial capital:

18 apple samples sold in a provincial capital were collected, and over 500 pesticide residues were screened by LC-Q-Orbitrap. 15 pesticide residues were detected in total 62 times frequency in 14 samples. The results are shown in Table 3.

TABLE 3

LC-Q-Orbitrap screening results for pesticide residues in apple samples from a provincial capital

| No. | Pesticide | Frequency |
|---|---|---|
| 1 | Acetochlor | 7 |
| 2 | Atrazine | 2 |
| 3 | Benalaxyl | 7 |
| 4 | Bromobutide | 6 |
| 5 | Butafenacil | 8 |
| 6 | Carboxin | 7 |
| 7 | Clomazone | 4 |
| 8 | Diazinon | 4 |
| 9 | Dimethachlor | 5 |
| 10 | Fenamiphos | 2 |
| 11 | Hexaconazole | 3 |
| 12 | Metconazole | 3 |
| 13 | Mevinphos | 1 |
| 14 | Omethoate | 2 |
| 15 | Pirimicarb | 1 |
| total | | 62 |

Example 2

Example of LC-Q-Orbitrap screening and confirmation techniques for over 500 pesticide (as described above) residues in lemon.

The sample pre-treatment, LC-Q-Orbitrap operation conditions and pesticide residues screening process can be referred to Example 1.

The LC-Q-Orbitrap screening result of lemon samples of a provincial capital:

13 lemon samples sold in a provincial capital were collected, and over 500 pesticide residues were screened by LC-Q-Orbitrap technique. 9 pesticide residues were detected in total 53 times frequency in above 10 samples. The specific results are shown in Table 4.

TABLE 4

LC-Q-Orbitrap screening results for pesticide residues in lemon samples from a provincial capital

| No. | Pesticide | Frequency |
|---|---|---|
| 1 | Amicarbazone | 7 |
| 2 | Bupirimate | 8 |
| 3 | Fenazaquin | 7 |
| 4 | Malathion | 6 |
| 5 | Picoxystrobin | 8 |
| 6 | Thiazopyr | 7 |
| 7 | Thiodicarb | 4 |
| 8 | Triazophos | 1 |
| 9 | Trifloxystrobin | 5 |
| total | | 53 |

Example 3

Example of LC-Q-Orbitrap screening and confirmation techniques for over 500 pesticide (as described above) residues in cabbage.

The sample pretreatment, LC-Q-Orbitrap operation conditions and pesticide residues screening process can be referred to Example 1.

The LC-Q-Orbitrap screening result of cabbage samples of a provincial capital:

25 cabbage samples sold in a provincial capital were collected, and over 500 pesticide residues were screened by LC-Q-Orbitrap.18 pesticide residues were detected in total 121 times frequency in 21 samples. The specific results are shown in Table 5.

Table 5 LC-Q-Orbitrap screening results for pesticide residues in cabbage samples from a provincial capital

TABLE 5

LC-Q-Orbitrap screening results for pesticide residues in cabbage samples from a provincial capital

| No. | Pesticide | Frequency |
|---|---|---|
| 1 | Benalaxyl | 7 |
| 2 | Cadusafos | 8 |
| 3 | Clomazone | 7 |
| 4 | Dimethachlor | 6 |
| 5 | Fenamiphos | 2 |
| 6 | Octhilinone | 4 |
| 7 | Orbencarb | 4 |
| 8 | Paclobutrazol | 9 |
| 9 | Penconazole | 8 |
| 10 | Pirimicarb | 5 |
| 11 | Pretilachlor | 10 |
| 12 | Prometon | 5 |
| 13 | Pyrazophos | 3 |
| 14 | Pyriproxyfen | 12 |
| 15 | Simazine | 15 |
| 16 | Sulfotep | 1 |
| 17 | Tebuthiuron | 4 |
| 18 | Trifloxystrobin | 11 |
| total | | 121 |

The above detailed description is provided only to specifically describe some feasible embodiments of the present invention rather than limit the protection scope of the present invention. Any equivalent embodiment or modification implemented without departing from the spirit of the present invention shall be deemed as falling into the protection scope of the present invention.

The invention claimed is:

1. An electronic ID database for pesticide compounds in edible agro-products based on LC-Q-Orbitrap, comprising various pesticide compounds electronic ID, which contains pesticide compound information, retention time, adduct ions information, fragment ions information, collision energies and optimal full scan mass spectrum; wherein the pesticide compound information includes the compound name and its molecular formula;

a retention time of the pesticide compound under specific chromatography and mass spectrometry condition is acquired by LC-Q-Orbitrap equipment under Full MS/dd-MS$^2$ mode, adduct ions in forms of $[M+H]^+$, $[M+NH_4]^+$, $[M+Na]^+$ under ESI source and pesticide compound molecular formula are determined, accurate mass number of pesticide compound adduct ions is obtained;

full scan mass spectrum under different normalized collision energies are acquired, and an optimal full scan spectrum with abundant ions information is selected, the optimal full scan mass spectrum refers an abundance ratio of adduct ions is 10%-20%, 3 to 5 fragment ions having a largest ion abundance ratio in the optimal full scan mass spectrum are selected, and a collision energy value is recorded;

the fragment ions information includes theoretical accurate mass number and an abundance ratio of fragment ions in the optimal full scan mass spectrum;

the ion abundance ratio is a signal strength ratio between fragment ion and a signal strongest fragment ion; and the database is ordered according to the retention time of the electronic ID.

2. The electronic ID database according to claim 1, wherein the database includes intelligent matching model, the intelligent matching model adds intelligent matching value $P_m$, in the electronic ID, is calculated according to the following equation:

$$P_m = W_b M_b + W_q \cdot \sum_{i=1}^{n-1}(M_i \cdot W_i);$$

$$W_i = \frac{I_i - I_{i+1}}{I_1 - I_{n-1}};$$

$$W_b + W_q = 1;$$

wherein $M_b$ is the theoretical accurate mass number value of adduct ion, $M_i$ is an accurate mass number value of the $i^{th}$ fragment ion, $W_i$ is a weight of the $i^{th}$ fragment ion, $I_i$ is an ion abundance ratio of $i^{th}$ fragment ion, order of fragment ions is descending according to the abundance ratio, $W_b$ is a weight of the adduct ion, $W_q$ is a comprehensive weight of fragment ions, and n is a number of fragment ions.

3. The electronic ID database according to claim 2, wherein the values of $W_b$, $W_q$ are adjusted according to the intelligent matching model, generally $W_b = W_q = 0.5$.

4. The electronic ID database according to claim 1, wherein the method to confirm theoretical accurate mass number of fragment ions is:

1) according to a compound molecular formula, the element composition of fragment ion is identified;

2) according to a mass number M of the fragment ion in the mass spectrum, a possible element composition list of the fragment ion is obtained by calculation according to the following equation:

$$M = \sum_{i=1}^{n} X_i y_i$$

wherein, $X_i$ is an accurate mass number of the $i^{th}$ fragment ion, n is an element number of fragment ion, $y_i$ is a number of corresponding elements in the $i^{th}$ fragment ion, 3) through a molecular structure cracking mechanism, selecting a reasonable fragment ion element composition from a list of fragment ion element composition, and theoretical accurate mass number M' is calculated according to the following equation:

$$M' = X_1 y'_1 + X_2 y'_2 + \ldots + X_n y'_n$$

wherein, $X_1, X_2 \ldots X_n$ are the accurate mass number of the fragment ion elements, $y'_1, y'_2 \ldots y'_n$ are the numbers of the corresponding elements of preferred fragment ion element composition.

5. The electronic ID database according to claim 1, wherein the chromatography mass spectrometry conditions are:

chromatographic conditions: separation through liquid chromatography system, which is equipped with reversed phase column (Accucore aQ 150×2.1 mm, 2.6 μm); mobile phase solution A: 5 mM ammonium acetate-0.1% formic acid-water; mobile phase solution B: 0.1% formic acid-methanol; gradient elution program: 0 min: 1% B, 3 min:30% B, 6 min: 40% B, 9 min: 40% B, 15 min: 60% B, 19 min: 90% B, 23 min: 90% B, 23.01 min: 1% B, post run for 4 min. flow rate: 0.4 mL/min; column temperature: 40° C.; and injection volume: 5 μL;

mass spectrometry conditions: scan mode: Full MS/dd-MS$^2$; Full MS mass scan range:70-1050 m/z; resolution: 70,000, Full MS; 17,500, MS/MS; AGC: Full MS, 1e6; MS/MS, 1e5; max IT: Full MS, 200 ms; MS/MS, 60 ms; loop count: 1; MSX count: 1; isolation width: 2.0 m/z; NCE (Stepped NCE): 40(50%); under fill ratio: 1%; apex trigger: 2-6 s; dynamic Exclusion: 5 s; and the mass spectrometry results is collected and processed by software TraceFinder.

6. A detection method for a pesticide compound in edible agro-products based on LC-Q-Orbitrap, comprising the steps of:

1) a sample to be tested is homogenized by acidified acetonitrile, dehydrated, centrifuged, concentrated, and then purified by solid phase extraction column (SPE), and the residual pesticide is eluted by acetonitrile+toluene, and concentrated and filtered to prepare a sample solution to be tested;

2) a chromatogram and mass spectrum of the sample solution are acquired under specific chromatography and mass spectrometry conditions by LC-Q-Orbitrap under Full MS/ddMS$^2$ mode to obtain a retention time, accurate mass number information of adduct ion, fragment ions and mass spectrum under corresponding optimal collision energy and record unknown compounds electronic ID corresponding to the retention time;

3) the unknown compounds electronic ID is sequentially compared with each pesticide compound electronic ID in an electronic ID database, if $\Delta T \leq 0.3$ and $\Delta P \leq 10\%$, the pesticide compound is recorded, otherwise the unknown compounds electronic ID is compared with a next pesticide compound electronic ID information;

4) after detection is completed, information of the pesticide contained in the test sample solution will be displayed;

wherein, $\Delta T$ is an absolute value of difference between the retention time of unknown compound and that of any pesticide compound in the database according to the following equation:

$$\Delta P = \frac{|P_c - P_i|}{\min(P_c, P_i)}$$

wherein, $P_c$ is an intelligent matching value of the unknown compound, $P_i$ is an intelligent matching value of the any pesticide compound in the database.

7. The detection method for according to claim 6, wherein in step 4 if $\Delta T \le 0.3$ and $10\% < \Delta P \le 30\%$, whether the pesticide compound is included or not is judged by a comparison of height and overlap ratio of the mass spectrum peak in the mass spectrum.

8. The detection method for according to claim 6, wherein:

the sample also includes the following pretreatment:

weigh 10.0 g (accurate to 0.01 g) of sample to 100 mL centrifuge tube, add 30 to 40 mL of 1% acidified acetonitrile (v/v) to extract, homogenize at 10,000 to 11,000 rpm for 1 to 2 min, add anhydrous magnesium sulfate and sodium chloride (mass ratio 4/1), the centrifuge tube was shaken for 8-10 min, and then centrifuged at 4200 rpm for 5 to 7 min, take 15 to 20 mL of supernatants into 150 mL heart-shaped bottle, and evaporate to 1 to 2 mL on a rotary evaporator at 40° C. water bath for clean-up; CarbonNH$_2$ column was used, add 1 to 2 cm anhydrous sodium sulfate in CarbonNH$_2$ column, SPE purification column was prewashed with 5 to 6 mL of acetonitrile/toluene solution, tap purification column gently to remove bubbles, discard the effluent under the purification column, when the liquid level is slightly above the top of sodium sulfate, transfer the concentrate to the purification column with a 50 ml heart-shaped bottle under it, the heart-shaped bottle was rinsed with 2 to 3 mL of acetonitrile/toluene solution, and decanted it to the purification column, repeat 2 to 3 times, the purification column was connected with a 25 mL reservoir and eluted with 25 to 30 mL of acetonitrile/toluene solution, the entire volume of effluent was collected and concentrated to 0.5 ml, and then evaporated it to dryness by nitrogen, finally, after adding 1 mL of acetonitrile/water solution, it was sonicated and filtered through a 0.22 μm nylon membrane.

* * * * *